United States Patent [19]
Larson et al.

[11] Patent Number: 5,752,926
[45] Date of Patent: May 19, 1998

[54] ORTHOPEDIC CASTS

[75] Inventors: Andrew W. Larson, Palo Alto; Steven P. Bitler, Menlo Park; Lawrence C. Greene, Boulder Creek; David D. Taft, Atherton; Ray F. Stewart, Redwood City; Valentine Y. Yoon, Redwood Shores; Thomas W. Ross, Los Gatos; David A. Kamp, Sunnyvale; Edward E. Schmitt, Palo Alto, all of Calif.

[73] Assignee: Landec Corporation, Menlo Park, Calif.

[21] Appl. No.: 150,683

[22] Filed: Nov. 9, 1993

Related U.S. Application Data

[63] Continuation-in-part of Ser. No. 92,351, Jul. 14, 1993, abandoned, and a continuation-in-part of Ser. No. 875,776, Apr. 29, 1992, abandoned.

[30] Foreign Application Priority Data

Apr. 28, 1993 [WO] WIPO ............... PCT/US93/03962

[51] Int. Cl.⁶ ...................................... A61F 5/01
[52] U.S. Cl. ............... 602/7; 602/21; 602/22; 602/26; 602/27; 428/34.5; 428/34.9; 428/35.2; 428/36.1; 428/36.4; 428/36.5; 428/36.8; 428/36.9; 428/36.91; 428/137; 428/158; 428/220; 428/230; 428/253; 428/254; 428/913; 524/92.1; 264/DIG. 71

[58] Field of Search .................. 602/6–8, 12, 22, 602/21, 26, 27; 428/34.9, 36.8, 34.5, 230, 131, 137, 138, 253, 254, 913, 220, 36.1, 36.5, 36.9, 36.91, 35.2, 36.4; 523/105, 111; 524/921; 264/230, DIG. 71; 138/137, 141, 146, 153

[56] References Cited

U.S. PATENT DOCUMENTS

| | | | |
|---|---|---|---|
| 2,616,418 | 11/1952 | Eberl ........................................... | 602/7 |
| 2,759,475 | 8/1956 | Swaay ........................................ | 128/90 |
| 3,243,211 | 3/1966 | Wetmore ..................................... | 403/28 |
| 3,332,416 | 7/1967 | Brickman et al. ......................... | 128/91 |
| 3,515,798 | 6/1970 | Sievert ....................................... | 174/135 |
| 3,582,457 | 6/1971 | Barthell ...................................... | 138/140 |

(List continued on next page.)

FOREIGN PATENT DOCUMENTS

| | | |
|---|---|---|
| 0003845 | 9/1979 | European Pat. Off. . |
| 0029727 | 6/1981 | European Pat. Off. . |
| 0086686 | 8/1983 | European Pat. Off. . |
| 0110860 | 6/1984 | European Pat. Off. . |
| 0169037 | 1/1986 | European Pat. Off. . |
| 0295031 | 12/1988 | European Pat. Off. . |

(List continued on next page.)

OTHER PUBLICATIONS

PCT Written Opinion dated Jul. 20, 1994.

Aharoni, S. M., "Rigid Backbone Polymers. 2. Polyisocyanates and their Liquid–crystal Behavior," *Macromolecules*, 12:94–103 (1979).

Andruzzi, F., et al., "Studies on Comb–like Polymers. 2. Poly(octadecylethylene oxide)," *Macromolecules*, 13:15–18 (1980).

(List continued on next page.)

*Primary Examiner*—Rena Dye
*Attorney, Agent, or Firm*—Jeffrey G. Sheldon; Timothy H. P. Richardson; Sheldon & Mak

[57] ABSTRACT

Orthopedic casts which comprise an elastically deformed support which is held in its elastically deformed state by a solid casting composition. After the cast has been placed around a patient's limb, it is heated to soften the casting composition, thus permitting recovery of the cast into conforming contact with the limb. The support can for example be a fabric knitted from elastomeric fibers and glass fiber yarns. The casting composition can for example comprise polycaprolactone and/or a side chain crystallizable polymer, which melts at 45°–60° C. A padded liner can be placed between the cast and the limb. Recovery of the cast is preferably carried out by means of a hot air gun.

39 Claims, 2 Drawing Sheets

U.S. PATENT DOCUMENTS

| | | | |
|---|---|---|---|
| 3,597,372 | 8/1971 | Cook | 523/300 |
| 3,669,824 | 6/1972 | Hess | 428/212 |
| 3,692,023 | 9/1972 | Phillips et al. | 428/138 |
| 3,728,206 | 4/1973 | Buese | 428/138 |
| 3,809,600 | 5/1974 | Larson | 428/131 |
| 3,898,369 | 8/1975 | Clabburn | 174/36 |
| 3,908,644 | 9/1975 | Neinart et al. | 602/8 |
| 3,968,791 | 7/1976 | Forsberg | 602/8 |
| 3,985,128 | 10/1976 | Garwood et al. | 602/8 |
| 4,019,505 | 4/1977 | Wartman | 602/7 |
| 4,035,534 | 7/1977 | Nyberg | 428/34.9 |
| 4,052,282 | 10/1977 | Kubushiro | 602/8 |
| 4,070,746 | 1/1978 | Evans et al. | 29/450 |
| 4,105,025 | 8/1978 | Wang et al. | 602/6 |
| 4,135,015 | 1/1979 | Boyden, Jr. et al. | 428/373 |
| 4,135,553 | 1/1979 | Evans et al. | 138/141 |
| 4,143,655 | 3/1979 | Custer et al. | 602/7 |
| 4,168,192 | 9/1979 | Nyberg | 156/86 |
| 4,175,177 | 11/1979 | Potts | 528/354 |
| 4,179,320 | 12/1979 | Midgley et al. | 156/86 |
| 4,193,395 | 3/1980 | Gruber | 602/7 |
| 4,207,364 | 6/1980 | Nyberg | 138/141 |
| 4,226,230 | 10/1980 | Potts | 602/7 |
| 4,231,356 | 11/1980 | Usukura | 602/8 |
| 4,238,522 | 12/1980 | Potts | 427/2.1 |
| 4,240,415 | 12/1980 | Wartman | 602/7 |
| 4,273,115 | 6/1981 | Holland et al. | 602/7 |
| 4,286,586 | 9/1981 | Potts | 602/7 |
| 4,287,012 | 9/1981 | Midgley et al. | 156/86 |
| 4,326,509 | 4/1982 | Usukura | 602/7 |
| 4,404,333 | 9/1983 | Watanabe et al. | 525/437 |
| 4,410,009 | 10/1983 | Blum | 138/109 |
| 4,427,003 | 1/1984 | Fennimore et al. | 602/8 |
| 4,433,680 | 2/1984 | Yoon | 523/111 |
| 4,442,833 | 4/1984 | Dahlen et al. | 602/8 |
| 4,473,671 | 9/1984 | Green | 523/105 |
| 4,483,333 | 11/1984 | Wartman | 602/7 |
| 4,498,467 | 2/1985 | Kirkpatrick et al. | 602/8 |
| 4,631,098 | 12/1986 | Pithouse et al. | 428/34.9 |
| 4,661,535 | 4/1987 | Borroff et al. | 523/105 |
| 4,668,563 | 5/1987 | Buese et al. | 428/230 |
| 4,708,130 | 11/1987 | Grudem | 602/19 |
| 4,784,123 | 11/1988 | Robeson | 602/8 |
| 4,793,330 | 12/1988 | Honeycutt et al. | 602/8 |
| 4,803,103 | 2/1989 | Pithouse et al. | 428/34.9 |
| 4,816,309 | 3/1989 | Hutt et al. | 428/34.9 |
| 4,821,708 | 4/1989 | Guignard et al. | 607/7 |
| 4,912,174 | 3/1990 | Grouiller | 525/415 |
| 4,940,047 | 7/1990 | Richter et al. | 602/6 |
| 4,946,726 | 8/1990 | Sandvig et al. | 428/76 |
| 4,951,656 | 8/1990 | Gorka et al. | 602/7 |
| 5,014,403 | 5/1991 | Buese | 28/170 |
| 5,016,622 | 5/1991 | Norvell | 602/7 |
| 5,016,624 | 5/1991 | Garrett et al. | 602/7 |
| 5,027,804 | 7/1991 | Forsyth et al. | 602/7 |
| 5,151,315 | 9/1992 | Ponnet | 428/212 |
| 5,256,134 | 10/1993 | Ingham | 602/8 |
| 5,334,442 | 8/1994 | Okamoto et al. | 428/246 |

FOREIGN PATENT DOCUMENTS

| | | |
|---|---|---|
| 0317180 | 5/1989 | European Pat. Off. . |
| 0338815 | 10/1989 | European Pat. Off. . |
| 0358451 | 3/1990 | European Pat. Off. . |
| 2417524 | 9/1979 | France . |
| 60-163662 | 8/1985 | Japan . |
| 1522399 | 11/1975 | United Kingdom . |
| 1560179 | 12/1976 | United Kingdom . |
| 2140429 | 5/1983 | United Kingdom . |
| 2125803 | 8/1983 | United Kingdom . |
| 8802636 | 4/1988 | WIPO . |
| 8807847 | 10/1988 | WIPO . |
| 8908463 | 9/1989 | WIPO . |
| 9013420 | 11/1990 | WIPO . |
| 9014060 | 11/1990 | WIPO . |
| 9109909 | 7/1991 | WIPO . |
| 9307194 | 4/1993 | WIPO . |

OTHER PUBLICATIONS

Chupov, et al., "Structure and Physico–chemical Properties of Comb–like Polypeptides Based on Poly–L–Lysine," *Polymer Science U.S.S.R.*, 21:241–252 (1979).

González de la Campa, J. I., et al., "Side–Chain Crystallinity, Heat of Melting, and Thermal Transitions in Poly [N–(10–η–Alkyloxycarbonyl–η–Decyl)Maleimides] (PEMI)," *J. Poly. Sci.*, Poly. Phys. Ed., 18:2197–2207 (1980).

Greenberg, S. A. et al., "Side Chain Crystallization of η–Alkyl Polymethacrylates and Polyacrylates," *J. Am. Chem.*, 76:6280–6286 (1954).

Jordan, Jr., E. F., et al., "Side–Chain Crystallinity. I. Heats of Fusion and Melting Transitions on Selected Homopolymers Having Long Side Chains," *Polymer Journal*, 9:1835–1852 (1971).

Jordan, Jr., E. F., et al., "Side–Chain Crystallinity. II. Heats of Fusion and Melting Transitions on Selected Copolymers Incorporating η–Octadecyl Acrylate or Vinyl Stearate," *J. Poly Sci.*, Part A–1, 9:3349–3365 (1971).

Jordan, Jr., E. F., et al., "Side–Chain Crystallinity. III. Influence of Side–Chain Crystallinity on the Glass Transition Temperatures of Selected Copolymers Incorporating η–Octadecyl Acrylate or Vinyl Stearate," *J. Poly Sci.*, Part A–1, 9:3367–3378 (1971).

Jordan, Jr., E. F., "Side–Chain Crystallinity. V. Heats of Fusion and Melting Temperatures on Monomers whose Homopolymers Have Long Side Chains," *J. Poly. Sci.*, Poly. Chem. Ed., 10:3347–3366 (1972).

Magagnini, P. L., et al., "Studies on Comb–like Polymers. Poly(octadecylethylene)" *Macromolecules*, 13:12–15 (1980).

Miyauchi, et al. "A New Composite Resistor with PTC Anomaly," *J. Polymer Sci.*: Polymer Chem. Ed., 19:1871–1873 (1981).

Overberger, C. G., et al., "The Preparation and Polymerization of ρ–Alkylstyrenes. Effect of Structure on the Transition Temperatures of the Polymers," *J. Am. Chem. Soc.*, 75:3326–3330 (1953).

Pittman, A. G., et al., "Effect of Polymer Crystallinity on the Wetting Properties of Certain Fluoroalkyl Acrylates," *J. Poly Sci.*, Part A–1, 7:3053–3066 (1969).

Platé, N. A., et al., "Comb–like Polymers. Structures and Properties," *J. Polymer Sci.: Macromolecular Reviews*, 8:117–253 (1974).

Rabolt, J. F., et al., "Studies of Chain Conformational Kinetics in Poly(di–η–alkylsilanes) by Spectroscopic Methods, 1. Poly(di–η–hexylsilane), Poly(di–η–heptylsilane), and Poly(di–η–octylsilane)," *Macromolecules*, 19:611–616 (1986).

Wada, T., et al., "Effect of Amount of Medium on the Radiation–induced Polymerization of Ethylene in tert–Butyl Alcohol," *J. Poly Sci.*, Part A–1, 10:1655–1667 (1972).

Watanabe, J., et al., "Thermotropic Polypeptides. 2. Molecular Packing and Thermotropic Behavior of Poly(L–glutamates) with Long η–Alkyl Side Chains," *Macromolecules*, 18:2141–2148 (1985).

Yokota, K., et al., "Widely–spaced Comb–like Polymers Having Fluoroalkyl Side Chains," *Polymer Journal*, 17(9):991–996 (1985).

PCT Search Report, dated Aug. 20, 1993.

5,752,926

1

ORTHOPEDIC CASTS

This application is a continuation-in-part of patent application Ser. No. 08/092,351, filed Jul. 14, 1993, by Stewart, Yoon, Larson, Ross, Greene, Kamp and Schmitt (Docket No. 9218.1) now abandoned, and of patent application Ser. No. 07/875,776 filed Apr. 29, 1992, by Stewart, Larson and Yoon (Docket No. 9218), now abandoned, and claims priority under 35 USC 119 and 365 from International Application No. PCT/US93/03962 filed Apr. 28, 1993 (Docket No. 9218.1-PCT). This application is also related to patent application Ser. No. 08/450,407 filed May 25, 1995, which is a divisional of this application. The disclosure of each of those four applications is incorporated herein by reference.

BACKGROUND OF THE INVENTION

This invention relates to orthopedic casts.

It is well known to make orthopedic casts, splints, supports, braces, shields, wound covers, and like orthopedic devices (all of which are referred to herein simply as "casts") from calcined gypsum (Plaster of Paris), from a polymer which is formed into shape while hot and hardens on cooling, or from a prepolymer which is formed into shape and then polymerized in situ, e.g. a polyurethane prepolymer which is hardened by water. The term "casting composition" is used herein to denote a polymeric composition which can be formed into shape around a substrate (referred to herein simply as a limb) and then hardened by chemical reaction or by cooling. Known casting compositions can comprise a single polymer or a mixture of two or more polymers, and can contain additional ingredients such as inorganic fillers, and can be associated with a flexible support, which may be elastic, for example a fabric or a foam sheet. Reference may be made for example to U.S. Pat. Nos. 3,692,023 (Phillips), 3,728,206 (Buese), 3,809,600 (Larson), 4,019,505 (Wartman), 4,105,025 (Wang), 4,193,295 (Gruber), 4,231,356 (Usukura), 4,273,115 (Holland), 4,326,509 (Usukura), 4,404,333 (Watanabe), 4,433,680 (Yoon), 4,473,671 (Green), 4,483,333 (Wartman), 4,643,909 (Kammerer), 4,668,563 (Buese), 4,784,123 (Robeson), 4,912,174 (Grouiller), 4,937,145 (Dull), 4,946,726 (Sandvig), 4,951,656 (Gorka), and 5,027,804 (Forsyth), European Patent Publication Nos. 0086686, 0110860, 0169037, 0338815 and 0358451, and PCT Publication Nos. WO 90/14060 and 91/09909. The disclosure of each of those documents is incorporated herein by reference.

All the known methods of making casts require excessive time, skill and care for good results. Prepolymers offer advantages over Plaster of Paris, but the use of water is messy and inconvenient, and frequently results in undesirable wetting of bandages and cast linings. Thermoplastic compositions avoid the use of water, but compositions which can be molded around the patient, at temperatures which do not harm the patient, do not have satisfactory properties in the final cast. Elastic supports for the casting composition, which are stretched as they are wrapped around the patient, lead to variable results, with excessive and/or insufficient pressure, even when very skillfully applied.

SUMMARY OF THE INVENTION

We have discovered a number of important improvements in casting compositions and in the construction, application and use of orthopedic casts, especially on human patients, but also on animals. These discoveries can also be utilized in equivalent and related fields, where the same or similar casts are applied to inanimate substrates and where the casting compositions are used for molding generally.

This application claims the novel orthopedic casts that we have discovered, and the divisional application U.S. Ser. No. 08/450,407 claims the novel methods of forming orthopedic casts around patients that we have discovered.

In a first aspect, this invention provides a a heat-shrinkable orthopedic cast which is preshaped and sufficiently oversize to allow it to be placed around a limb of a patient, and which comprises (1) a fabric support which
  (a) is in an elastically stretched condition, and
  (b) comprises elastic fibers which are
    (i) composed of an elastomeric material and
    (ii) elastically stretched; and
(2) a solid casting composition which
  (a) comprises a crystalline polymer having a crystalline melting point $T_m$ which is at least 40° C. and no more than 60° C.,
  (b) contacts the fabric support and maintains it in its elastically stretched condition, and
  (c) when the cast is heated to a temperature above $T_m$ after the cast has been placed around a limb of a patient, softens into an amorphous state and permits shrinkage of the cast towards the limb without exposing the patient to a temperature which cannot be safely tolerated by the patient; and said cast, when heated to a temperature above $T_m$ and permitted to shrink in the absence of any restraint, having at least one dimension which shrinks by more than about 5% based on that dimension prior to heating, at least some of the shrinkage of the cast, when it is heated, being provided by elastic shrinkage of the elastically stretched fibers of the fabric support.

In a second aspect, this invention provides a heat-shrinkable orthopedic cast which is preshaped and sufficiently oversize to allow it to be placed around a limb of a patient, and which comprises (1) a heat-shrinkable main member which comprises
  (a) a fabric support which
    (i) is in an elastically stretched condition, and
    (ii) comprises elastic fibers which are composed of an elastomeric material and are elastically stretched, and
  (b) a solid casting composition which
    (i) comprises a crystalline casting polymer having a crystalline melting point, $T_m$, of 40° C. to 85° C.,
    (ii) contacts the support and maintains it in its elastically stretched condition, and
    (iii) when the cast is heated to a temperature above $T_m$, softens and permits shrinkage of the heat-shrinkable main member, at least some of the shrinkage of the main member being provided by elastic shrinkage of the elastically stretched fibers, and
(2) a liner which comprises padding material and is secured to the inside of the main member.

We have found that the presence of a liner, in accordance with the second aspect of the invention, increases the maximum temperature which the casting composition can reach during the application of the cast, and thus broadens the range of compositions which can be used without danger of harming the patient. The presence of the liner also increases the reliability with which a satisfactory cast can be prepared, apparently because the liner helps to provide a uniform pressure between the recovered cast and the limb, and does so more effectively than a similar material which is applied to the limb before the heat-recoverable cast is placed around the limb.

In a third aspect, this invention provides a heat-shrinkable orthopedic cast which is preshaped and sufficiently oversize to allow it to be placed around a limb of a patient and which, after being placed around the limb, can be heated so that it shrinks towards the limb, the cast comprising (1) a heat-shrinkable main member which comprises
 (a) a fabric support which
  (i) is in an elastically stretched condition, and
  (ii) comprises elastic fibers which are composed of an elastomeric material and are elastically stretched, and
 (b) a solid casting composition which comprises
  (i) a crystalline casting polymer having a crystalline melting point Tm, of 40° to 85° C.,
  (ii) contacts the support and maintains it in its elastically stretched condition, and
  (iii) when the cast is heated to a temperature above $T_m$, softens and permits shrinkage of the heat-shrinkable main member, at least some of the shrinkage of the main member being provided by elastic shrinkage of the elastically stretched fibers, and
(2) a flexible reinforcing component which (a) does not prevent shrinkage of the main member, (b) has been applied to the main member, and (c) comprises a polymer precursor which can be polymerized to form a relatively rigid component.

The third aspect of the invention is directed to a preferred embodiment of one of our discoveries, namely that the properties of a heat-recovered cast (whether or not it includes a liner as described above) can be further improved by providing a flexible component on at least part of the outside surface of the cast, and then treating the component to make it relatively rigid. The flexible component can be for example a prepolymer which is polymerized in situ. Such a prepolymer can be applied to the exterior of the heat-recoverable cast, in which case it is preferably selected so that it remains unchanged during the recovery process and does not substantially impede the recovery. Alternatively, the prepolymer can be applied to the recovered cast. In either case, the recovered cast provides a barrier between the limb and water or other reagents used to assist in polymerizing the prepolymer. The flexible component can also be a thermoplastic casting composition which (a) is applied hot to the outside of the recovered cast, or (b) is applied cold to the outside of the recovered cast and is then heated in place. The heat-recovered cast provides an effective thermal barrier between the flexible thermoplastic component and the limb, thus making it possible to use thermoplastic casting compositions having relatively high melting points. When a flexible component is used in this way, the physical properties of the finished composite cast depend on both the heat-recovered component and the hardened component. Indeed, the heat-recovered cast can serve primarily as a mold for the flexible component and make only a small contribution to the physical properties of the finished composite cast.

The term "transition point" is used herein to denote either a crystalline melting point ($T_m$) or a glass transition point ($T_g$). The term "soften" is used herein to denote softening of the casting polymer as it undergoes crystalline melting or as it passes through a glass transition.

A preferred method of making an orthopedic cast comprising a reinforcing component comprises (A) providing an elastically deformable support;
(B) contacting the support, while it is elastically deformed, with a casting composition which comprises a casting polymer having a transition point $T_s$ and which is at a temperature above $T_s$;
(C) cooling the casting composition to a temperature below $T_s$ to produce a heat-recoverable main member wherein the casting composition maintains the support in an elastically deformed condition; and
(D) providing on the main member a flexible reinforcing component which can be subjected to a treatment which will reduce its flexibility.

In this method, the hot casting composition is preferably applied to the support after the support has been elastically deformed, e.g. over a form. However, it is also possible to apply the casting composition to the support while the support is in its relaxed state, and then to stretch the coated support, with heating before, during or after the stretching. The reinforcing component can be provided at any convenient stage. For example, it can be placed on the support before or after the support is elastically deformed; it can be applied before or after the casting composition, or be a part of the casting composition; it can be provided on all or on selected part(s) of the main member, including parts which are not contacted by the casting composition; and it can be present as a continuous or intermittent coasting or as a separate, e.g. a self-supporting, film. The support can be a sheet or a tape, but is preferably of closed cross-section, particularly a tube, thus providing a cast of closed cross-section which can if desired be modified by cutting, e.g. to a desired shape or to provide a cast of open cross-section. Alternatively, the support can be a sheet or a tape which is formed into a cast of closed cross-section at any convenient stage of the process. For example, a heat-recoverable sheet or tape can be wrapped around a form and the outer end secured to the wrapped material beneath it. The reinforcing component can be provided on the sheet or tape before it is wrapped, or as it is wrapped, or after it has been wrapped.

BRIEF DESCRIPTION OF THE DRAWINGS

The invention is illustrated in the accompanying drawings, in which.

DETAILED DESCRIPTION OF THE INVENTION

Definitions, Abbreviations and Measurements

Figure 1:
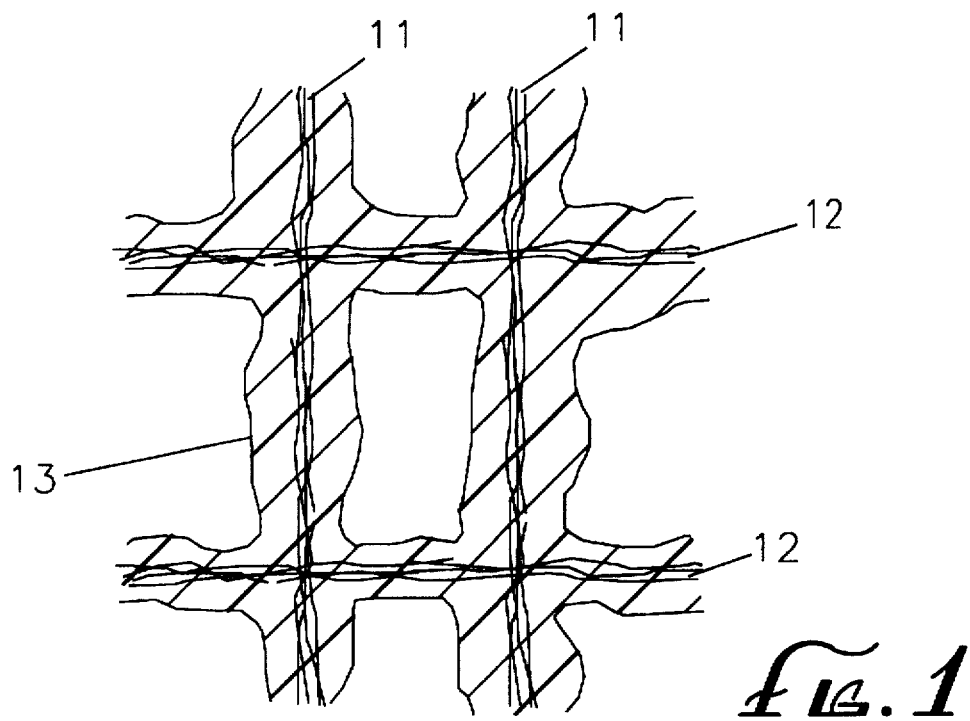
FIG. 1 is a cross-section through a part of a cast of the invention.

In this specification, parts, amounts and percentages are by weight. Temperatures are in °C. Molecular weights are weight average molecular weights expressed in Daltons and are determined by gel permeation chromatography (GPC) in tetrahydrofuran (THF). First order transition points (often referred to as melting points), glass transition points, and heats of fusion are determined by a Differential Scanning Calorimeter (DSC) using the second heat cycle and a heating rate of 10° C./minute. The softening point, $T_m$, for crystalline polymers is the peak of the DSC curve. Crystallization temperatures are determined by a DSC at a cooling rate of 10° C./minute.

The "power" of a material is defined as the force required to stretch a 1-inch (2.54 cm) wide sample of the material to twice its original length. Melt Index values are measured by ASTM D1238 (modified). Tensile modulus values are calculated according to ASTM D638 after testing the material by ASTM D1708 at a crosshead speed of 1 inch/minute (2.54 cm/minute). Strength values given herein are the tensile modulus of the material (psi) multiplied by the thickness of the material (inch). Strength values for casts above $T_m$ are measured after heating the material to $(T_m+10)°$ C. and allowing it to equilibrate at that temperature for 5 minutes. Strength values for molded casts are measured at 25° C. after heating the cast to at least $(T_m+10)°$ C., allowing the cast to recover without any restraint (if it is heat-recoverable), cooling it to 25° C. and allowing the cast to equilibrate at 25° C. for 1 hour. Air flow permeability (AFP) values given herein are measured as follows. An air gun is secured in a jig, and an anemometer is placed in a reference position at the center of the air stream at a distance of 5 inch (12.7 cm) from the tip of the gun. The gun is adjusted so that the air is cold and the air flow recorded by the is about 1700 ft/min (570 m/min). A flat sample of the heat-recoverable member or the liner (or a corresponding sample—see below) in the shape of a circle 2 inch (5.1 cm) in diameter, or a larger sample, is placed across the air flow at right angles to the air flow, at a distance of 5 inch (13 cm) from the tip of the gun. The air flow is recorded by the anemometer at three different spots within about 0.5 inch (1.2 cm) of the reference position, and is averaged. The AFP of the cast is the average air flow, expressed as a percentage of the air flow without the cast. Since the sample must be flat, and the heat-recoverable member, both before and after molding, are usually not flat, it is usually necessary to measure AFP values on corresponding samples, i.e. on sheets obtained by flattening out a portion of the cast, taking care not to change its porosity, or on sheets which are flat but which have otherwise been prepared in the same way as the heat-recoverable member. For example, after measuring the AFP of an unused sample using cold air, the air gun can be adjusted to provide hot air which will effect recovery of the sample, and the AFP of the recovered sample can be measured.

Crush strengths of casts are measured on an Instron 1122 tensile tester by placing the cast between the plates of a crushing jig and forcing the plates together at room temperature.

Heat-recoverable Main Members

The casts of the invention, before use, contain heat-recoverable main members whose heat-recoverability results at least in part from the presence of an elastomeric support which is maintained in an elastically deformed (usually stretched) condition by the casting composition, and which recovers towards an undeformed configuration when the casting polymer is softened by heating. The casts can also be heat-recoverable at least in part because the casting polymer, and/or a support which forms part of the cast, is composed of a crosslinked polymer which has been deformed above its melting point, and cooled in the deformed condition; such a material, when heated above its melting point, will tend to return to its undeformed condition.

The available recovery of the main member will depend on the extent of the deformation put into it. Preferably the main member, if heated in the absence of any restraint, will recover so that at least one dimension thereof decreases from a first value x to a second value y, where y is at most 0.95x, particularly at most 0.75x, i.e. shrinks by at least 5%, particularly at least 25%. It is generally unnecessary for y to be less than 0.4x, and in most cases y is more than 0.45x. The strength (including the crush strength) of the recovered main member depends not only on the support and the casting polymer and the dimensions and amounts thereof, but also on the extent of the recovery and the heating used. It is often desirable to continue the heating for a short while after recovery of the main member, e.g. for another 1 to 3 minutes, in order to consolidate the cast.

Casting Polymers

The casting compositions used in this invention contain a casting polymer having a transition point $T_s$, preferably a crystalline melting point $(T_m)$ of at least 40° C., particularly at least 45° C., especially at least 48° C., to ensure that the cast does not soften under normal atmospheric conditions. $T_s$ should also be such that the casting polymer will soften and permit recovery at temperatures which do not cause distress to human patients. When the cast includes a liner which acts as a thermal barrier to the heat applied to the cast to cause its recovery, $T_s$ can be for example as high as 85° C., but is preferably not more than 70° C. When no such liner is present, $T_s$ is preferably no more than 60° C., particularly no more than 55° C. Softening preferably takes place over a range of less than 20° C., particularly less than 15° C., especially less than 10° C., more especially less than 5° C. If the casting polymer is a polyolefin, it preferably consists essentially of a single tactic form, i.e. is wholly atactic or syndiotactic or isotactic, so that its melting point is sharp. It is preferred that rehardening should take place rapidly on cooling from above $T_s$ to below $T_s$, so that the patient does not have to remain still for an extended time while the cast hardens; we have found that excellent results are obtained in practice if, when the cast is heated above $T_s$ and then cooled to $(T_s 10)°$ C. at a rate of 10° C./min, the casting polymer rehardens not more than 2 minutes, preferably not more than 1 minute, after it has cooled to $T_s$. When a liner is used, casting polymers having $T_s$'s above 55° C., e.g. polycaprolactone-based compositions, can be used without causing distress to the patient, and are often preferred because of their ready availability. Suitable polycaprolactone-based casting polymers include compositions disclosed in the documents incorporated herein by reference. The polycaprolactone preferably has a $T_m$ of about 55° C. to about 60° C., and a molecular weight of 20,000 to 80,000, particularly 30,000 to 60,000. Examples of such polycaprolactones which are commercially available include the product sold by Solvay Interox Chemicals (Warrington, Great Britain) under the trade name CAPA-640, which has a reported molecular weight of about 37,000 and a $T_m$ of about 57° C., and the product sold by Union Carbide (Danbury, Conn., USA) under the trade name Tone 767E, which has a reported molecular weight of about 40,000 and a $T_m$ of about 55° C.

Also preferred for use as casing polymers in the present invention, particularly when the heat-recoverable cast does not include a liner, are crystalline polymers in which the crystallinity results exclusively or predominantly from side chains which are attached to the polymer backbone. Such polymers are often referred to as side chain crystallizable polymers, or SCCs, and include polymers containing units derived from (or derivable from) one or more monomers such as substituted and unsubstituted acrylates, fluoroacrylates, vinyl esters, acrylamides, maleimides, a-olefins, p-alkyl styrenes, alkylvinyl ethers, alkylethylene oxides, triglycerides (e.g. tristearin and pentaerythritol tetrastearate), alkyl phosphazenes and amino acids; polyisocyanates; polyurethanes; and polysiloxanes; as described for example in J. Poly. Sci. 60, 19 (1962), J. Poly. Sci. (Polymer Chemistry) 7, 3053 (1969), 9, 1835, 3349, 3351, 3367, 10, 1657, 3347, 18, 2197, 19, 1871, J. Poly. Sci. Macromol. Rev. 8, 117 (1974), Macromolecules 12, 94 (1979), 13, 12, 15, 18, 2141, 19, 611, JACS 75, 3326 (1953), 76; 6280, Polymer J 17, 991 (1985); and Poly. Sci USSR 21, 241(1979).

SCC's for use as casting polymers in this invention can be broadly defined as polymers which comprise repeating units of the general formula

where Y is an organic radical forming part of a polymer backbone and Cy comprises a crystallizable moiety and is preferably present in amount such that the SCC has a heat of fusion of at least 20, preferably at least 40, Joules/gram. The crystallizable moiety may be connected to the polymer backbone directly or through a divalent organic or inorganic radical, e.g. an ester, amide, carbonyl, carboxy, amino, hydrocarbon (for example phenylene), ether or thioether link, or through an ionic salt linkage (for example a carboxyalkyl ammonium, sulfonium or phosphonium ion pair). The radical Cy may be aliphatic or aromatic, for example alkyl of at least 10 carbons, fluoralkyl of at least 6 carbons or p-alkyl styrene wherein the alkyl contains 6 to 24 carbons. The SCC may contain two or more different repeating units of this general formula. The SCC may also contain other repeating units, but the amount of such other units is preferably such that the total weight of the crystallizable moieties is at least twice the weight of the remainder of the polymer.

Preferred SCC's comprise side chains containing in total at least 5 times as many carbon atoms as the polymer backbone, particularly side chains comprising linear polymethylene moieties containing 12 to 50, especially 16 to 22, carbon atoms. The SCC may also contain units derived from one or more other monomers, e.g. other alkyl acrylates, methacrylates (e.g. glycidyl methacrylate), acrylamides and methacrylamides; acrylic and methacrylic acids; acrylamide; methacrylamide; maleic anhydride; 2-isocyanatoethyl methacrylate; comonomers containing amine groups, styrene; vinyl acetate; monoacrylic functional polystyrene; ethyl vinyl ether; vinyl chloride; hydroxyalkyl acrylates and methacrylates; alkoxyalkyl acrylates and methacrylates; and derivatives of polyethylene glycol with molecular weights from 50 to 5,000. Such other monomers are generally present in total amount less than 50%, particularly less than 35%, especially less than 25%, e.g. 0 to 15%. They may be added to modify the melting point, modulus, MVTR, or other physical properties of the SCC, or to provide sites for crosslinking.

One example of an SCC is an SCC consisting essentially of units derived from 0–100% hexadecyl acrylate (C16A), 0–100% octadecyl acrylate (C18A) and 0–20% of one or more of acrylic acid, methacrylic acid, itaconic acid, maleic anhydride or a similar monomer providing a cure site on the copolymer.

The SCC may also be reacted with one or more other materials which produce a strengthened material, for example a multifunctional agent such as amine-terminated propylene oxide, polyethylene oxide, polytetrahydrofuran and polybutadienes containing hydroxyl groups, di-, tri- or multifunctional acrylic or methacrylic esters, vinyl ethers, esters and amides, isocyanates, aldehydes and epoxies.

The SCC may also be reacted with another polymer, or formed on another polymer, so that it is present as one of the blocks in a block copolymer. Such block copolymers are described for example in International Patent application No. PCT/US92/08508 filed Oct. 6, 1992 and copending commonly assigned U.S. Application Ser. No. 08/048,280 (Docket No. 9213.2) filed Apr. 14, 1993, the disclosures of which are incorporated herein by reference. An SCC polymer as described above can provide the hard block, with the soft block being provided by an amorphous block having a $T_g$ less than $(T_m-10)°$ C. or a crystalline block (which may also be an SCC block) having a melting point $T_{ms}$ less than $(T_m 10)°$ C. Alternatively, an SCC polymer as described above can provide the soft block, with the hard block being provided by an amorphous block having a $T_g$ greater than $(T_m+10)°$ C. or a crystalline block having a melting point $T_{mh}$ greater than $(T_m+10)°$ C. Suitable amorphous blocks are well known in the art and include polyethers, polystyrene, polyacrylates, polyesters and polyurethanes.

Particular examples of casting compositions include the following, which are novel per se:
  (I) Compositions which comprise
    (A) a random copolymer which comprises
      (i) at least 30% of units having a crystalline melting point (in the copolymer) of $T_m°$ C. and derivable from at least one n-alkyl acrylate or n-alkyl methacrylate wherein the n-alkyl group contains 14 to 50 carbon atoms, and
      (ii) 7 to 70% of units derived from at least one monomer, said monomer being one which, when homopolymerized, results in a homopolymer having a glass transition point $T_g$ which is at least $(T_m+10)°$ C., and
    (B) a random copolymer which comprises
      (i) at least 30% of units derived from ethylene and
      (ii) 7 to 70% of units derived from an ethylenically unsaturated monomer containing at least one polar group,
    the ratio of A to B being from 0.25 to 4.
  (II) Compositions which comprise
    (A) an SCC polymer which has a molecular weight of less than 15,000 and which contains 2 to 10%, preferably 3 to 7%, of units derived from acrylic or methacrylic acid, and
    (B) an ethylene/vinyl acetate copolymer which contains 25 to 40% of units derived from vinyl acetate, and preferably also 2 to 10% of units derived from acrylic or methacrylic acid.
  (III) Compositions which comprise
    (A) 30 to 90% of at least one SCC polymer having a crystalline melting point $T_m$ (in the composition) of 40 to 60° C., and
    (B) 10 to 70% of at least one amorphous polymer which (i) contains a plurality of groups which react with the SCC polymer, and (ii) has a molecular weight of 1,000 to 20,000, e.g. a polyether, particularly a polyether selected from polyethylene oxide, polypropylene oxide and polytetrahydrofuran.
  (IV) Compositions which comprise
    (A) 30 to 70% of at least one SCC polymer having a molecular weight of 2,000 to 200,000, and
    (B) 25 to 70% of at least one polymer which (i) has a melt index of 2 to 200 and (ii) is selected from polycaprolactone and copolymers consisting of units derived from ethylene and vinyl acetate and optionally from one or more other comonomers.

These novel compositions are also useful for other purposes, for example as temperature-sensitive coatings, e.g. on seeds, as packaging materials, as molding compounds, and as hot melt adhesives.

The molecular weight of the casting polymer is generally more than 5,000, and when it is the sole polymeric ingredient of the casting composition is preferably at least 50,000, for example 60,000 to 300,000, particularly at least 100,000, for example 140,000 to 200,000. When the casting polymer is a block copolymer containing SCC blocks, its molecular weight is preferably more than 25,000, especially more than 75,000, with the molecular weight of each SCC block preferably being 2,500 to 20,000.

The casting polymer can be crosslinked by radiation or chemical crosslinking methods known to those skilled in the art. Radiation crosslinking can be effected, for example, by an electron beam or Cobalt 60 radiation. Chemical crosslinking can be effected, for example, by means of peroxides or silanes, by ionic crosslinking, or with the aid of multifunctional agents.

Casting Compositions

The casting compsition can contain, in addition to the casting polymer of transition point $T_r$, one or more additional polymers and/or one or more non-polymeric ingredients, e.g. inorganic fillers, plasticizers, antioxidants, processing aids, and pigments, for example carbon black, graphite, glass fibers, Kevlar fibers, silica, titanium dioxide, talc, magnesium carbonate and calcium carbonate.

Conventional SCC polymers tend to have poor physical properties, and this limits their value as casting polymers. SCC block copolymers and strengthened or crosslinked SCC polymers have better physical properties, but require additional preparative steps. We have discovered that improved physical properties can be obtained by blending the SCC polymer with an appropriate additional polymer. The resulting compositions are useful not only as casting polymers but also for other purposes, e.g. as hot melt adhesives, packaging materials, seed coatings, etc.

We have obtained particularly good results by making use of an SCC polymer which contains at least 30% of units derivable from at least one n-alkyl acrylate or methacrylate in which the n-alkyl group contains 14 to 50, preferably 18 to 30, especially 20 to 24, carbon atoms and 7 to 65%, preferably 9 to 60%, especially 18 to 42%, of units derived from a high $T_g$ monomer, i.e. a monomer which, if homopolymerized, gives a polymer having a $T_g$ which is at least $(T_m+10)°$ C., preferably at least $(T_m+20)°$ C., especially at least 80° C., but which is preferably not more than 120° C. particularly not more than 100° C. The preferred high $T_g$ monomer is styrene; other high $T_g$ monomers include a-methyl styrene and other aromatic compounds containing vinyl groups, methyl methacrylate, ethyl methacrylate, t-butyl acrylate and phenoxy ethyl acrylate. The SCC can also contain up to 15%, preferably up to 10%, e.g. 2 to 7%, of units derived from other monomers, preferably acrylic acid. The molecular weight of the polymer is preferably 25,000 to 500,000, particularly 50,000 to 200,000. Such an SCC polymer can have a surprisingly high modulus, often more than 40,000 psi, (28,000 kg/cm$^2$), a sharp melting point, low melt viscosity and good recrystallization kinetics.

The properties of such an SCC polymer can be yet further improved, in particular its impact strength can be increased, by mixing with it a random ethylene copolymer which comprises at least 30% of units derived from ethylene and 7 to 70% of units derived from at least one ethylenically unsaturated monomer containing at least one polar group. The compatibility of these polymers is highly surprising. The ethylene copolymer is preferably an ethylene/vinyl acetate copolymer containing 16 to 60%, particularly 26 to 42% of units derived from vinyl acetate, and preferably also containing 2 to 10% of units derived from acrylic acid. The ratio of the SCC polymer to the ethylene polymer is preferably from 0.25 to 5, particularly 0.5 to 4.

The blends just described are particularly valuable examples of blends which comprise an SCC polymer and a second polymer which improves the physical properties of the SCC polymer. Thus we have discovered that improved physical properties can often be obtained by blending an SCC polymer with at least one compatible olefin polymer, especially an ethylene/vinyl acetate or ethylene/vinyl acetate/acrylic acid copolymer. Good results are obtained when the SCC polymer contains units derived from acrylic or methacrylic acid, preferably in amount 2 to 10%, particularly 3 to 7%, and has a molecular weight of less than 15,000, preferably less than 10,000, and the EVA polymer contains 25 to 50%, preferably 28 to 35% of units derived from vinyl acetete; particularly good results are obtained when the EVA polymer also contains units derived from acrylic or methacrylic acid, e.g. in amount 2 to 10%. Other olefin polymers which can give improved physical properties include other ethylene copolymers, including ethylene/vinyl chloride, ethylene/acrylic acid, ethylene/ethyl acrylate, ethylene/butyl acrylate, and ethylene/methyl acrylate copolymers. The mixture can also contain an ionic component, e.g. a zinc acrylic acid complex.

Another way in which the physical properties of SCC polymers can be improved is by blending them with polycaprolactone (PCL) or another cyclic ester polymer as disclosed in U.S. Pat. No. 3,692,023. Some PCL polymers and the related polyesters have melting points which are too high to permit their use in casts which are heated after application to the patient, even when a liner is used in accordance with the second aspect of the invention; they also take a long time to crystallize after cooling below $T_m$. However, we have found that mixtures of SCC polymers and PCL can have a $T_m$ substantially below that of the PCL on its own, without undue broadening of the melting range. Preferred SCC polymers for this purpose comprise units derived from C16A and/or C18A, and optionally units derivable from one or more other monomers selected from n-alkyl acrylates and methacrylates in which the alkyl group contains less than 18 carbons, acrylic acid, methacrylic acid, acrylamide, and methacrylamide. Particularly preferred SCC polymers are C16A/C18A/AA copolymers.

As briefly indicated above, the casting compositions can contain a wide variety of fillers and other non-polymeric ingredients. However, we have found that certain fillers give better results than others, in particular in improving the modulus and/or elongation of the composition, or the balance between modulus and elongation, particularly with casting compositions containing an ethylene/vinyl acetate copolymer in addition to an SCC casting polymer. We have obtained particularly good results through the use of calcium carbonate (both untreated and surface-treated), wollastonite (acicular calcium silicate) and talc (magnesium silicate).

Supports

The supports used in the present invention are elastically deformable. The support preferably has, in the main member before it is recovered, an open structure which assists in the heat transfer between different parts of the main member, and which, in the finished cast, remains sufficiently porous to ensure that the support has a high moisture vapor transmission rate (MVTR) and thus does not prevent the limb from "breathing". When a support in a heat-recoverable cast has an open structure, the size of the apertures therein will decrease during recovery. Recovery will also make the support more rigid. Thus the cross-sectional area of the components of the support will normally increase during recovery, and previously separated components will come closer together and be bonded together by the casting polymer. The support preferably comprises an elastic material which is held in an elastically deformed state by the solid casting polymer, but which recovers towards an undeformed state when the casting polymer softens. Alternatively, the support can be a crosslinked polymeric article which has been deformed above its melting point and cooled in the deformed state, thus rendering the article heat-recoverable if it is again heated above its melting point.

The support is preferably elastically deformable. In a fabric, elasticity can result from the construction of the fabric and/or the inherent elasticity of the fibers therein. For example, a support which can be used in this invention can be a knitted fabric prepared entirely from a glass fiber yarn. However, preferred supports are fabrics, particularly knitted fabrics, in which at least one of the yarns is composed of an elastomeric material. The fabric may be isotropic or have elasticity or other properties which vary directionally. Preferably the support can be stretched elastically in at least one direction by at least 25%, preferably at least 50%, e.g. 50 to 125%, based on the corresponding dimension of the support in its unstretched state. For example, the support can be a knitted, woven or braided material which comprises an elastomeric yarn, e.g. a segmented polyurethane yarn, or a natural or synthetic rubber yarn, preferably with a high strength nonelastomeric yarn, e.g. a glass fiber, graphite, polyamide or polyarylene yarn, which is selected to give the cast desired strength or other physical properties. Suitable support materials are described for example in US Pat. No. 4,668,563 (Buese), and are available commercially, for example nylon/segmented polyurethane fabrics and glass fiber/segmented polyurethane fabrics. The power of the fabric is preferably 0.1 to 2.0 lb/inch (18 to 360 g/cm). The support preferably has, at least after stretching, an open structure, so that the coated support (i.e. the cast) can also have an open structure, as further described elsewhere in this specification.

Heat-Recoverable Main Members

The recovery forces in the main member should be sufficient to ensure adequate conformance of the cast to the limb, but not so high as to damage the patient, or cause pain, or reduce blood flow. The power of the cast, in the direction of recovery, is, therefore, preferably 0.1 to 2.0 lb/inch (18 to 360 g/cm).

Part or all of the interior surface of the casts of the invention can be coated with an adhesive. The adhesive can be for example a temperature-activated adhesive as described in International Application No. PCT US90/02223 (Docket No. 9433.1-PCT), or a pressure-sensitive adhesive (PSA), for example a PSA as disclosed in International Patent Application No. PCT US92/01153 (Docket No. 9211.1-PCT) filed Feb. 12, 1992, claiming priority from US patent application Ser. No. 07/829,494 filed Feb. 12, 1991, or in US application Ser. No. 08/048,280 (Docket No. 9213.2) filed Apr. 14, 1993, particularly a PSA containing an SCC polymer additive which reduces the adhesive strength of the PSA when the PSA is warmed. The use of such an adhesive is often particularly desirable when the cast surrounds a finger and needs to resist removal by the patient (such casts are often referred to as "Mallet Finger" casts) by laminating such a sheet to a support.

When the cast comprises a sheet of the casting composition or is made by laminating such a sheet to a support, the sheet is generally 1 to 5 mm thick, with smaller thicknesses, e.g. less than 2 mm, being preferred for smaller casts, e.g. for fingers, toes and hands.

We have found that the casts are much easier to apply, without overheating which can cause distress to the patient or the orthopedist, if the main member has, before recovery, an open structure which permits rapid and uniform heating of the casting composition, especially when using a hot air gun to heat the cast. Thus the main member, before recovery, preferably contains a plurality of apertures having an area of at least $0.01cm_2$, preferably at least $0.02cm_2$. The apertures should not be so large as to permit the limb to become overheated. When the cast includes a liner, the size of the apertures is preferably less than $0.12cm^2$, particularly less than $0.08cm^2$. When no liner is present, the size of the apertures is preferably less than $0.08cm^2$, particularly less than $0.06cm^2$. The size and number of the apertures are preferably such that over substantial areas of the heat-recoverable member, particularly over the whole of the casting polymer, heating the cast with a hot air gun causes a difference in temperature, between the inside and the outside of the heat-recoverable member at any particular point, of not more than 15° C. Preferably the main member has, before recovery, an air flow permeability (AFP) of at least 5%, more preferably at least 10%, particularly at least 20%, but less than 60% when a liner is present, and less than 45% when no liner is present, more preferably less than 35%. When an unused cast is molded into its finished state, any apertures therein will become smaller (or disappear completely) as a result of recovery and/or thermoplastic flow of the casting polymer. However, it is very desirable that the finished cast should retain a sufficiently open structure to allow the substrate to "breathe", i.e. should have a good moisture vapor transmission rate (MVTR). It is, therefore, preferred that the apertures in the unused cast should remain sufficiently large in the finished cast to provide this benefit. We have found that the AFP of the finished cast is preferably at least 1%, more preferably at least 2%, particularly at least 5%, especially at least 8%.. On the other hand, the larger the size and the number of apertures in the finished cast, the weaker and less water-resistant it will be. Preferably, therefore, the AFP of the finished cast is less than 25%, more preferably less than 20%, particularly less than 15%, especially less than 10%.

When a cast is prepared by laminating together two or more porous components, e.g. by wrapping 2, 3 or 4 thicknesses of a porous sheet material, the performance of the cast reflects the porosity of the individual components so that when a cast is prepared in this way, the sheet material preferably has an AFP of at least 15%, particularly at least 25%, but less than 60%, particularly less than 40%, especially less than 30%.

It is desirable that the cast should become relatively inflexible in a short period after molding is complete. Preferably, therefore, the casting composition, as it cools, changes from a moldable composition to a relatively stiff composition over a temperature range of less than 10° C., particularly less than 5° C., and preferably does so in less than 5 minutes, particularly less than 2 minutes. The casting polymer need not recover all of its crystallinity in order for the casting composition to become relatively inflexible. In this specification, the polymer can be regarded as having cooled to a crystalline relatively inflexible material if its crystallinity is at least 0.5 X, where X is the crystallinity of the polymer after it has been cooled from above $T_m$ to $(T_m-10)°$ C. and maintained at $(T_m-10)°$ C. for four crystallization half lives.

The main member preferably has a closed cross-section which is in approximately the desired final shape, but sufficiently oversize to allow the cast to be placed around the limb. However, to assist in fitting a cast to a limb, and/or to assist in its later removal, the cast may comprise at least one elastomeric component which is free of the casting composition and is elastically deformable before or after (preferably both before and after) the cast has been fitted around the substrate. The elastomeric component can be a longitudinal component which extends over part or all of the length of the cast, or a radial component which extends around part or all of the circumference of the cast. For example, the cast may comprise (1) a first component which (i) has an open cross-section and (ii) comprises the casting polymer, and (2) an elastomeric component which (i) forms a closed cross-section with the first component and (ii) is elastically deformable when the article is in its first (recoverable) configuration and/or when the article is in its second (fitted) configuration. The elastomeric component can be secured to the first component after the first component has been formed, or a casting polymer can be applied to part only of an elastomeric support. Alternatively or additionally, the cast can be in the form of two or more parts which can be fitted together around the substrate and secured together before heating begins. One or more of the component parts can carry means for securing the parts together, preferably means which permit the size of the cast to be adjusted, e.g. hook-and-loop closures of the kind sold under the trademark "Velcro". In addition, it should be understood that the invention also includes heat-recoverable articles, e.g. tapes, which can be used to make heat-recoverable casts of closed cross-section, e.g. by wrapping around a form to make a preformed cast or by wrapping around the limb itself.

Pre-shaped casts may have a wide variety of shapes, including for example a cylinder for use as a finger splint, a bent cylinder to surround an ankle, knee or elbow, or a glove to surround part or all of a hand.

Preparation of Casting Compositions and Heat-Recoverable Main Members

The casting compositions used in this invention can be prepared by mixing procedures well known in the art, and can be formed or applied to supports by procedures well known in the art, e.g. as solutions in organic solvents which are removed by drying, or as molten compositions, e.g. by melt extrusion onto the support or by hot lamination. The casting composition is preferably applied to the non-deformed support, and the composite then stretched e.g. over a mandrel or other form, while the casting composition is at a temperature above $T_s$ followed by cooling with the support in its stretched condition. Casts having similar shape but different strengths can readily be prepared by wrapping a cooled stretched tape over a form twice, or three times, or more than three times. The casting composition can also be applied to the stretched support and solidified on it. In both cases, at least one dimension of the support is generally stretched by 40 to 150% of its unstretched length (i.e. to 1.4 to 2.5 times its unstretched length), preferably 60 to 150%, for example 100 to 140%, of its unstretched length. After the composition has been applied to a support, it may be desirable to heat it, at a temperature well above $T_r$, preferably with pressure, to ensure that it fully penetrates the support. It may also be desirable to blow air through the casting composition to ensure that the open structure of a porous support is not filled up by the casting polymer. In many cases it is desirable that the heat-recoverable main member should be sufficiency flexible to be flattened, e.g. for ease of storage or to enable it to be cut to a desired shape.

Liners

When a liner is present, as is preferred, the liner provides a thermal barrier between the limb and at least part, preferably all, of the heat-recoverable main member while the main member is being recovered. Since the liner remains in place between the recovered cast and the limb, it must have satisfactory properties (e.g. permeability to water vapor) for this use. In the cast before it is recovered, the liner is preferably elastically deformed so that it fits snugly around the limb after the cast has been recovered. We have obtained excellent results with a liner which is elastically deformable and which has a plurality of apertures through its thickness such that it has an air flow permeability (in the undeformed state) of less than 25%. When, as is preferred, the main member has a plurality of apertures through its thickness, so that it can be more readily recovered by means of a stream of hot air, the liner preferably has an air flow permeability of less than 0.75 times the air flow permeability of the main member.

The liner preferably comprises a stockinette fabric, i.e. an elastically deformable circular knit fabric, preferably a circular rib knit fabric. The stockinette may for example comprise a natural or synthetic polymeric yarn, e.g. a cotton or other cellulosic yarn, or a polyester, polyamide or polypropylene yarn. The stockinette preferably has a fully recovered diameter which enables it to fit snugly around the limb to which the cast is applied. Suitable stockinette fabrics are well known in the art, for example for covering a limb before forming a cast around the limb. In the present invention, by contrast, the liner is secured to the main member so that it provides a thermal barrier between the limb and the heat-recoverable main member. The liner is preferably secured to the main member by means of end sections which pass around the ends of the main member and are secured to the outside of the main member, preferably by means of elastic forces generated by deforming the liner.

While the heat-recoverable main member is being heated in order to recover it, the ends of the liner are preferably unfolded so that they cover the parts of the patient adjacent to the area to be covered by the cast, thus providing a thermal barrier in these areas as well as underneath the cast.

The liner preferably comprises a padding material which is compressed between the limb and heat-recovered main member. Particularly when such padding material is present, a uniform pressure between the cast and the limb can readily be achieved. Suitable padding materials are typically non-woven fabrics of cotton (or other cellulosic) or polyester fibers, and are well known to those skilled in the art. Foamed polymers can also be used as padding material. Materials which combine an elastically deformable fabric and padding material are commercially available and can be used in this invention, including for example the product sold by Smith and Nephew Casting under the trade name ProTouch One-Step, which is a cotton/spandex stockinette having adhesively bonded to it polyester padding which permits the stockinette to expand without tearing the padding; the product sold by Balfour Health Care under the trade name Terry Rolls, which is an acrylic/spandex rib knit stockinette with acrylic loops on one surface only; and the product sold by Knit Rite under the trade name Cast-Rite, which is a thick acrylic/spandex circular knit stockinette fleeced on one surface only.

Reinforcing Components

In one preferred embodiment of the invention, a flexible reinforcing component is provided on at least part of the heat-recoverable member, and is treated to reduce its flexibility while the main member is being recover and/or after the main member has been recovered. The treatment will generally not affect the main member, but the invention includes reinforcing components and treatments which have separate effects on the reinforcing component and on the member and those which act jointly on the reinforcing component and the main member to strengthen the finished cast.

The flexible component can be applied to the main member at any appropriate stage, for example before the main member is stretched at all, after it has been stretched but before the casting polymer has been applied to it, while it is heat-recoverable (either as a heat-recoverable tape or as an article made by wrapping a heat-recoverable tape around a form), while it is being heat-recovered, or after it has been heat-recovered. There may be more than one reinforcing component, applied to the same or different parts of the main member, applied at the same or different stages, and consisting of the same or different materials.

When the reinforcing component is applied to the main member before the main member is recovered, it must not prevent, and preferably does not substantially change, recovery of the main member. Preferably it comprises a prepolymer (i.e. a mixture of monomers and/or oligomers which can be polymerized), and which can be treated, during and/or after recovery of the main member, to effect polymerization. The prepolymer can for example be applied as such or as part of a liquid composition, for example a solution of the prepolymer in a solvent which is at least partially evaporated before and/or during recovery of the main member. The prepolymer can also be applied in association with a substrate, e.g. a knitted, woven or non-woven fabric or netting, a polymeric film, or reinforcing fibers, provided that the substrate does not prevent recovery of the main member. The prepolymer can for example be supported by, e.g. impregnated into, an elastic support which is stretched over the heat-recoverable main member and which recovers towards a relaxed condition during heat-recovery of the main member. The treatment to effect polymerization can for example be to apply (e.g. spray) a chemical reagent, preferably water, and optionally a catalyst, to the prepolymer, or to expose the prepolymer to a catalyst and/or radiation which will effect polymerization thereof. When applied after recovery of the main member, the water or other chemical reagent can also serve to cool the heat-recovered cast. Particularly preferred prepolymers are polyurethane polymers which can be polymerized by the addition of water, and which typically are reaction mixtures of at least one polyol with a molar excess of at least one polyisocyanate so that the reaction mixture contains free isocyanate groups, generally 4 to 30%, preferably at least 5%, particularly at least 8%, free isocyanate groups. Suitable polyurethane prepolymers are disclosed, for example, in the documents incorporated herein by reference, and often include additional ingredients such as stabilizers (e.g. benzoyl chloride), anti foaming agents (e.g. polysiloxanes), viscosity modifiers, and catalysts (e.g. tertiary amines). We have found that casts with higher strengths are often obtained when the polymerization of the prepolymer takes place at the same time as the recovery of the main member. The heating which causes recovery of the main member increases the rate of polymerization and reduces the viscosity of the polymerization mix, which results in less foaming, as compared to a separate polymerization step after recovery of the main member.

When the flexible component is part of the heat-recoverable cast, it is important to store the cast under conditions which prevent the flexible component from becoming inflexible, for example in a moisture-impermeable envelope.

When the reinforcing component is applied to the cast after it has recovered, it is not necessary that the reinforcing component be one which does not impede recovery. Thus the flexible component can for example comprise a prepolymer as described above, and the prepolymer can optionally be coated onto or otherwise associated with a substrate, e.g. a knitted, woven or non-woven fabric or netting, a polymeric film, or reinforcing fibers, which, if present before recovery of the cast, would impede recovery of the cast. The substrate can for example be knitted or woven from glass fiber yarns, polypropylene yarns, or elastic yarns, or combinations thereof. When the reinforcing component is applied to the recovered cast, it is also possible for it to comprise a thermoplastic material, preferably a thermoplastic polymer, optionally coated onto or otherwise associated with a substrate, e.g. as just described for a prepolymer. Suitable thermoplastic materials include those already known for use as casting materials, including those disclosed in the documents incorporated herein by reference. A preferred material comprises polycaprolactone or a derivative thereof, optionally mixed with one or more other polymers. The thermoplastic material can be preheated and applied hot to the recovered cast, or laid onto, preferably wrapped around, the recovered cast and then heated in situ.

The reinforcing component can also be a second heat-recoverable cast. The second heat-shrinkable cast reinforces all or selected parts of the cast which has already been applied. It can also be used to improve the appearance of the cast and/or to cover the ends of a liner which have been folded back over the ends of the recovered main member. For example the reinforcing component can be a little shorter than the applied cast, so that it covers the extremities of the folded ends of the liner, but leaves a margin, e.g. of 0.5 to 2 inch.

Preferably at least a part of the main member lies between the reinforcing component and the limb to which the cast is applied. The main member can then act as a barrier between the limb and the reinforcing component, for example to provide a thermal barrier between the limb and a hot thermoplastic reinforcing component, or to prevent or reduce contact between the limb (and any bandages or dressings on the limb), and water or other reagent applied to harden a prepolymer.

When a reinforcing component is used, the reinforcing component is selected so as to enhance the physical and/or esthetic pities of the main member. Preferably the presence of the reinforcing component results in a finished cast whose crush strength is at least 1.5 times, particularly at least 2 times, the crush strength of a finished cast which is identical, and has been treated identically, except that it does not include the reinforcing component. Indeed the reinforcing component can supply almost any proportion of the crush strength of the finished cast. For example, the heat-softenable casting polymer can be used in an amount which is sufficient to maintain the support in its elastically deformed state but which makes little contribution to the strength of the finished cast. For example, the finished cast can have a crush strength which is more than 5 times, even more than 10 times, the crush strength of a finished cast which is identical except that it does not include the reinforcing component. In this embodiment of the invention, the main member can act principally as a form which, after it has molded to the shape of the limb, distributes the forces of the reinforcing component, particularly when the reinforcing component is supported on a sheet or tape, e.g. an elastic sheet or tape, which is wrapped around the recovered main member, and thus helps to ensure that no undue pressure is exerted on the limb.

Figure 2:
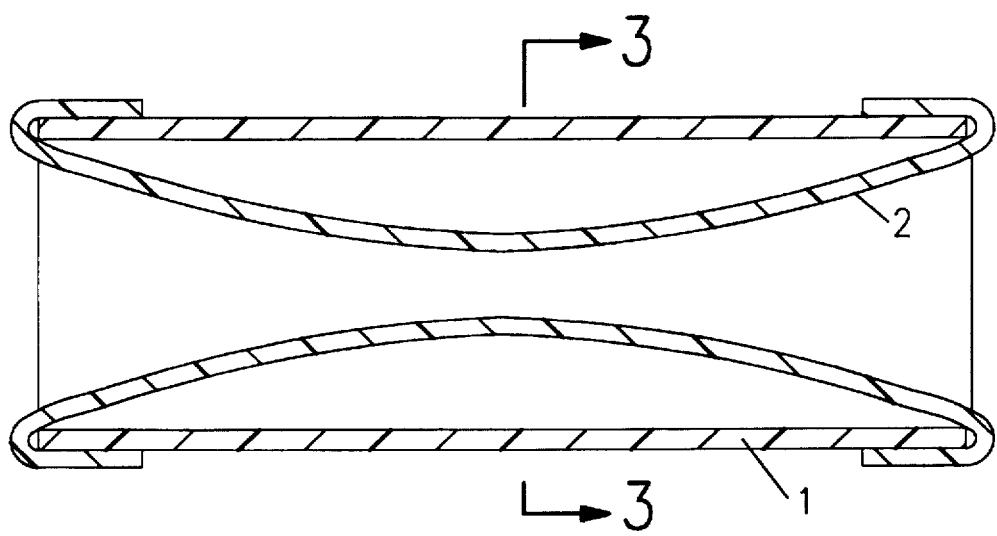
FIG. 2 is a diagrammatic longitudinal cross-section of a cast of the invention.
Figure 3:
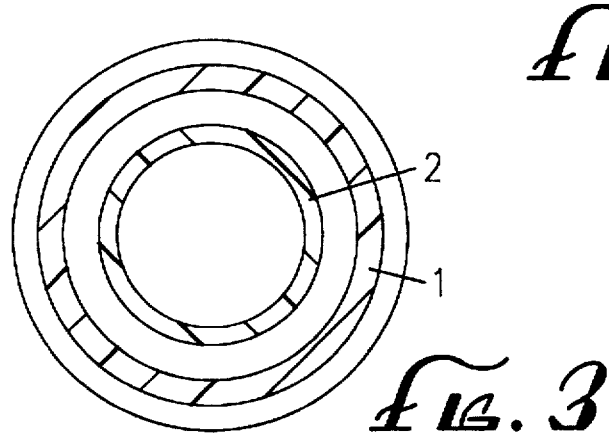
FIG. 3 is a transverse cross-section on line II—II of FIG. 2.
Figure 4:
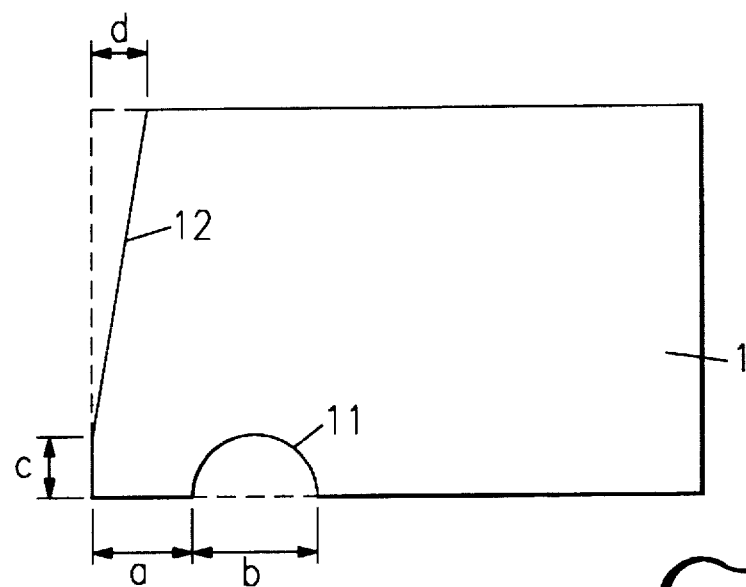
FIG. 4 is a plan view of a flattened heat-recoverable main member.
Figure 5:
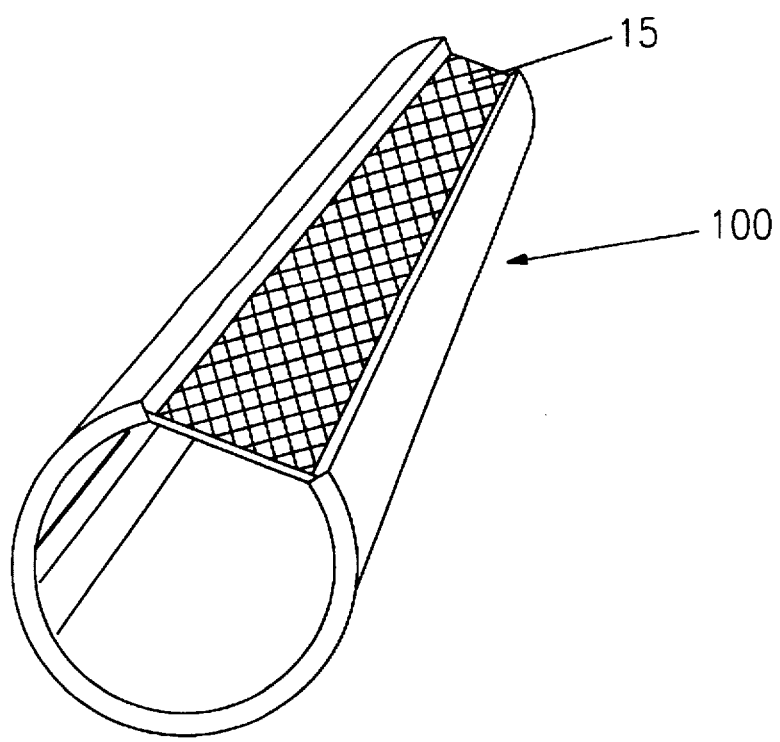
FIG. 5 is a diagrammatic view of a cast of the invention and having an elastomeric longitudinal component which is not coated by the casting composition.

Referring now to the drawings, FIG. 1 is a diagrammatic cross-section through a cast of this invention, and shows elastomeric yarns 11 and 12 which are maintained in a stretched condition by solid casting polymer 13. FIGS. 2 and 3 are diagrammatic longitudinal and transverse cross-sections of a cast of this invention which includes a heat-recoverable main member 1 and a padded stockinette liner 2. The main member comprises multiple wraps (usually 2 or 3) of the support, which is held in an elastically deformed condition by the casting composition. The ends of the liner 2 are folded back over the ends of the main member. FIG. 4 is a diagrammatic plan view of a flattened heat-recoverable main member 1 which is suitable for use as an arm cast. A main member in the form of a cylinder has been flattened and then cut so as to produce a thumb hole 11 of diameter b at an axial distance a from one corner of the member. In addition, starting at a radial distance c from the same corner and ending at an axial distance d below the opposite corner, the end of the cylinder has been cut off along line 12, so that the member will conform better to the palmer creases of the hand. FIG. 5 shows a cylindrical cast 100 with an elastomeric non-coated longitudinal component 15.

EXAMPLES

This invention is illustrated in the following Examples.

Examples 1–34

In Examples 1 to 34, the following abbreviations are used to refer to the compounds and materials set out in parentheses after the abbreviation: AA (acrylic acid), C4A (butyl acrylate), C14A (tetradecyl acrylate), C16A (hexadecyl acrylate), C18A (octadecyl acrylate), C22A (docosanyl acrylate), MMA (methyl methacrylate), C4MA (butyl methacrylate), C18MA (octadecyl methacrylate), GMA (glycidol methacrylate), ETGMA (ethyl triglycidol methacrylate), STY (styrene), C12SH (dodecyl mercaptan), XAMA (a polyfinctional crosslinking agent sold by Hoechst Celanese under the trade name Xama 2), ESP570 (t-amylperoxy 2-ethyl hexanoate), ESP 5100 (t-amylperoxy benzoate), JT and JD (polyfunctional amines sold by Texaco under the trade names Jeffamine T-3000 and Jeffamine D-4000, respectively), PCL (polycaprolactone sold by Polymer Sciences under the trade name PCL640),.ELV40, ELV 150, ELV240, ELV250, ELY4260 and ELV4320 (different grades of ethylene/vinyl acetate copolymers sold by E. I. duPont de Nemours under the trade names Elvax 40, Elvax 150, Elvax 246, Elvax 250, Elvax 4260 and Elvax 4320 respectively), EY901 and EY902 (different grades of ethylene/vinyl acetate copolymers sold by Quantum Chemical Co. Inc. under the trade names Vynathene EY901-25 and EY 902-35 respectively), HEP (heptane), TOL (toluene), NL Knit (a knitted fabric which contains about 85% polyhexamethylene adipamide (nylon) fibers and about 15% segmented polyurethane (Lycra) fibers, has a thickness of about 0.023 cm (0.015 inch) and a weight of about 95g/m$^2$, has a linear stress strain curve at extensions up to about 126%, and exhibits a power of about (0.75 lb/inch), GLF (0.75) and GLF (2.0) (E-type non-woven random glass fiber mats which have weights of about 0.022, 0.044 and 0.06g/cm$^2$ (0.75, 1.5 and 2.0 oz/sq ft) respectively, sold by Tap Plastics), GRAPH (a non-woven graphite mat sold under the trade name Panex CPF by Stackpole), GL Knit (a warp knitted fabric which contains glass fiber yarn and an elastic yarn, which has a weight of about 530 g/m$^2$, and which is available from Carolina Narrow Fabric Co., Winston-Salem, N. C., USA), DAB9 (calcium carbonate sold by United Minerals Co. under the trade name DAB9), W-30 (Wollastonite sold by R. T. Vanderbilt Co. under the trade name W-30), and Nytal (talc sold by R. T. Vanderbilt under the trade name Nytal 400).

SCC Polymers

The first step in Examples 1–34 was to make SCC polymers S1 to S23, using the monomers and amounts thereof specified in Table 1 below. The monomers were placed in a vessel with a suitable solvent, and optionally with azobisisobutyronitrile (AIBN) as an initiator and/or C12SH as a chain transfer agent. These ingredients were heated under nitrogen, with stirring, at an elevated temperature, e.g. 60–70° C., for an appropriate time, e.g. 12–20 hours. After cooling, the SCC polymer was precipitated by pouring the reaction mixture into ethanol. For example, in preparing polymer S1, the monomers and 0.5 g AIBN were dissolved in 150 mL toluene, and heated at 70° C. for 12 hours. In preparing polymers S3–S11, the monomers were dissolved in sufficient toluene to give a reaction mixture containing 42% monomers, and the reaction mixture was heated at 60° C. for 16 hours. In preparing polymer S12, the monomers, 0.05 g C12 SH, and 3.5 g AIBN were dissolved in a mixture of 1400 mL heptane and 80 mL ethyl acetate, and the reaction mixture was heated at 60° C. for 20 hours. In preparing polymer S20, 1700 g of a mixture of C22 A, STY, AA and C12 SH (ratio 60/37/3/0.19) was maintained at 105° C. while adding a blend of the same mixture (6800 g) and ESP570 (42.5 g) over 90 mins; ESP 5100 (42.5 g) was then added over 45 mins, while raising the temperature to 140° C.; and this temperature was maintained for a further 230 minutes. Polymers S21–23 were made in a similar way.

Examples 1–15

In Examples 1 to 15, the next step was to prepare the fabric support, using the fabric designated in Table 2 and as further described below. The fabric support was then contacted with a composition containing the ingredients and amounts thereof set out in Table 2 and processed as further described below.

Example 1

The NL Knit fabric was sewn into a tube of diameter about 1.6 cm (0.63 inch) having maximum elasticity in the radial direction. The fabric tube was fitted over a mandrel of diameter 1.9 cm (0.75 inch), and was then coated with the SCC polymer composition, which also contained 25 parts of heptane as solvent. After the solvent had been removed by heating, the weight of polymer deposited on the fabric was about 1 g. per inch of the tube measured in the axial direction. The coated tube was removed from the mandrel and retained its expanded shape. It could be easily deformed, for example by pressing into a flat sleeve. Two 7.6 cm (3 inch) lengths were cut from the tube. One length was placed over a finger, and then heated with a hair dryer, causing it to shrink and fit snugly over the finger. The second length was placed over the first, and likewise shrunk. After 2 minutes, the two lengths had hardened into a composite cast which immobilized the finger but did not restrict its blood flow. The cast was later reheated, when it became soft and flexible, so that it could be removed, or the finger and cast could be repositioned into a different shape, e.g. a bend; after two minutes the cast had again cooled and hardened, immobilizing the finger in its new shape.

Example 2

A strip of the NL Knit fabric was stretched about 50% and coated with the SCC polymer composition, heated at 90° C.

for 2 hours, and cooled. A first sample of the resulting flexible coated fabric was wrapped around a finger and then heated; the fabric softened and shrank snugly around the finger, and on cooling formed a rigid cast, with the overlapping parts of the fabric adhering to each other, which immobilized the finger but did not restrict its blood flow. A second sample was heated and then wrapped around a finger, using light tension; on cooling, the fabric formed a rigid cast which immobilized the finger but did not restrict its blood flow. A third sample was used in the same way as the first, but greater tension was used when wrapping; on cooling, the resulting cast was uncomfortably tight, and restricted blood flow.

Example 3

In each of Examples 3A, 3B and 3C, the dry SCC polymer was placed on top of the GLF fabric, and the fabric and polymer were heated between sheets of siliconized release paper in a press at 100° C. and 14 kg/cm$^2$ (100 psi). The ratio by weight of fabric to polymer was about 1.5. The resulting composites were stiff at temperatures below about 39° C., but flexible at temperatures above about 42° C.

Example 4

A sample of the composite of Example 3C, about 10×10 cm (4×4 inch), was laminated between two sheets of a polyester thermoplastic elastomer ("Hytrel" 4056) about 0.0025 cm (0.001 inch) thick. The laminate was cut into the shape of a nose splint, warmed with a hair dryer to make it flexible, and formed over a nose. After cooling, it provided a rigid nose splint.

Example 5

Another, larger, sample of the composite of Example 3C was laminated between 0.0044 cm (0.00175 inch) thick polyester film ("Medifilm 325" from Bertek) and a 0.0025 cm (0.001 inch) thick film of polymer S12, which is a temperature-responsive adhesive. The resulting composite was rigid and non-tacky at room temperature. It was cut into the shape of a Vilinus nose splint, warmed with a hair dryer to make it flexible and to make the adhesive tacky, and then formed over the nose and forehead of a person. After cooling, it provided a rigid splint bonded to the nose and forehead.

Example 6A

The NL Knit fabric was sewn into a tube about 91 cm (36 inch) long and about 1.4 cm (0.55 inch) in diameter. The outside of the tube was coated with the SCC polymer solution, which also contained toluene (30 parts), and then dried at 135° C. for 3 hours. The coating weight was about 95 g/m$^2$. The coated tube was cut into 10 cm (4 inch) lengths which were heated with a hot air gun to make them flexible and then expanded by 100% over a mandrel, and cooled on the mandrel. A first expanded length was placed over a finger and then heated with a hair dryer, causing it to shrink and fit snugly over the finger. A second expanded length was placed over the first and likewise shrunk, forming a composite cast which was significantly stronger than the cast produced in Example 1. A 2.5 cm (1 inch) length of the coated tube was cut lengthwise so that its mechanical properties could be measured. At 25° C., the fabric was inelastic and had a strength of about 1430 g/cm (8 lb/inch). At 50° C., the fabric had a power of about 204 g (0.45 lb), was reversibly elastic, and exhibited a linear stress/strain curve of about 100% elongation.

Example 6B

The NL Knit fabric, in flat sheet form, was coated with the SCC polymer solution and then dried at 135° C. for 3 hours. A 21.5×28 cm (8.5×11 inch) of the coated fabric was folded in half, and then cut and sewn so that it comprised a first tube about 10 cm (4 inch) long with a diameter of about 6.3 cm (2.5 inch), and a second tube about 6.3 cm (2.5 inch) long with a diameter of about 1.9 cm (0.75 inch) which communicates with the first tube and is at an angle of about 60° to it. This structure can be heated, expanded while hot, and cooled in the expanded state. The resulting structure is a cast which can be placed over a hand to cover the wrist, part of the palm of the hand and the thumb, and which, when heated with a hair dryer, shrinks and forms, after cooling, a rigid cast which immobilizes the thumb.

Example 7

One of the expanded lengths produced in Example 6 was lightly coated on the inside with a 30% solution of the S12 SCC polymer, which was a temperature-responsive adhesive. After it had been dried, the adhesive was non-tacky at room temperature. The adhesive-coated length was placed over a finger and then heated with a hair dryer, causing it to shrink and to form, after cooling, a rigid cast bonded to the finger.

Example 8

The graphite fabric was coated with the SCC composition, which also contained toluene (30 parts) and then dried at 140° C. for 2 hours. The coating weight was about 201 g/m$^2$ (0.132 g/inch$^2$). A coating about 0.0025 cm (0.001 inch) thick of the S12 SCC polymer adhesive was formed on a polyester thermoplastic elastomer ("Hytrel" 4056) film 0.0045 cm (0.00175 inch) thick. The coated fabric and the coated film were laminated together, with the SCC polymers in contact. To the other side of the graphite fabric was bonded a 0.0051 cm (0.002 inch) thick film of an acrylic pressure-sensitive adhesive sold by Monsanto Chemical as a solution under the trade name Gelva 737. The resultant composite was rigid at room temperature; when warmed with a hair dryer, became flexible and could be conformed around a substrate; and after cooling provided a rigid protective shell bonded to the substrate. For example, a 7.5×7.5 cm (3×3 inch) sample of the composite was used in this way to provide a rigid molded protective cast bonded to a person's heel.

Example 9

The blend of the S1 SCC polymer and the PCL was made by melt mixing at 100° C. The blend had a $T_m$ of 44° C. and a recrystallization temperature of 34° C.; a sample of it 7.6×10.1×0.076 cm (3×4×0.03 inch) could be warmed with a hair dryer to a temperature at which it was flexible, could be wrapped around a finger, and allowed to cool, when it formed a rigid cast around the finger. The PCL on its own had a $T_m$ of 60° C. and a recrystallization temperature of 23° C.; a similar sample of PCL on its own, when heated to a temperature at which it was flexible, could not be wrapped around a finger because the finger could not tolerate the heat.

Examples 10A and 10B

A sample of S3 SCC polymer was heated to 100° C. for 5 minutes and placed on a metal block maintained at 32° C. The SCC polymer began to harden after 20 seconds and was fully hardened after 60 seconds. The PCL polymer, similarly treated, began to harden after 90 seconds, and was not fully hardened until after 4 minutes.

Example 11

The blend of S1 SCC polymer and the PCL was made by melt mixing. The blend has a $T_m$ of about 42° C. The blend was hot melt coated onto the NL Knit fabric, and cooled. A sample about 7.5×10 cm (3×4 inch) was cut from the coated fabric; warmed in water at 60° C., thus rendering it flexible; and wrapped around a finger. After cooling for 3 minutes, it provided a rigid splint around the finger.

Example 12

The coated fabric of Example 3B was laminated between two sheets of polyurethane film 0.0044 cm (0.00175 inch) thick. ("Tuftane" 4056, sold by Lord Corporation, Erie, Pa.), each sheet being coated on its inner surface with a layer of an acrylic pressure-sensitive adhesive (Gelva 737). The resulting laminate was rigid at room temperature. However, by exerting sufficient force, it could be wrapped around a 0.63 cm (0.25 inch) mandrel, thus fracturing the rigid parts of the laminate, and making it possible to wrap the laminate around a person's wrist. The wrapped laminate was heated with a hair dryer, thus softening the laminate, and then allowed to cool, when it formed a rigid splint around the wrist.

Example 13

The solution of the SCC polymer (5 parts of one of the polymers S3 to S11 dissolved in 5 parts of toluene) was coated onto the NL Knit fabric so that the weight of the solution was 40–60% of the weight of the uncoated fabric and heated at 135° C. for 4 hours. The cooled composites were inelastic at room temperature, but were flexible and could be stretched by up to 50% when heated to 50° C. When the stretched composite was cooled to room temperature, it again became inelastic. For example, 2.5× 10.2 cm (1×4 inch) strips were stretched about 50% at 50° C.; cooled in the stretched state; loosely wrapped around a 1.25 cm (0.5 inch) mandrel; and heated to 50° C. The strips recovered, providing a rigid, protective coating conforming to the mandrel, with overlapping sections of the strips adhered to each other.

Example 14

Several 7.6 cm (3 inch) lengths were cut from the expanded tube of coated NL Knit fabric prepared in Example 6, and a layer of a medical grade pressure-sensitive adhesive in the form of a transfer tape ("Avery I-780" available from Avery Dennison) was applied to the outside of the lengths. Strips 2.5 cm (1 inch) wide were cut lengthwise from the lengths. These strips recovered when heated, and became inelastic when cooled. For example, one strip was applied to loose skin on a person's bicep. When the strip was heated with a hair dryer, it contracted, pulling under the strip together and uniformly stretching the surrounding skin. Thus a strip of this type can be applied over a wound or incision and, when desired, heated to close and protect the wound or incision. A strip of this type can also be used to stretch an area of skin, e.g. around a burn.

Example 15

The blend of S13 SCC polymer and Elvax 240 was made by melt mixing. The polymers appeared to be completely compatible in the melt. A sample of the blend was melt pressed to a thickness of about 0.0127 cm (0.005 inch), laminated to the NL Knit fabric at 100° C., and allowed to cool. The laminate was heated to 60° C., stretched 100%, and cooled in the stretched state. When reheated, the stretched fabric contracted, and on cooling became rigid.

In Examples 16 and 17, the composition designated in Table 2 was prepared and used in the way described below.

Example 16

The specified blends of SCC polymer and Elvax were prepared by melt mixing. In each of Examples 16A, B and D, the polymers appeared to be completely compatible, and the blend could be melted easily and molded on human skin to provide a protective coating. However, in Example 16C, the polymers were not compatible, and the blend did not soften sufficiently to be useful as an orthopedic device at temperatures which could be tolerated by human skin.

Example 17

The specified blends of S18 SCC polymer and Jeffamine in Examples 17A, B, C and D were made by melt mixing. 50 g samples of the S18 SCC polymer on its own (Example 17E) and of the blends (Examples 17A, B, C and D) were melt processed into plaques and heated under pressure for 4 hours at 150° C. At room temperature, Sample E was opaque and very brittle. Samples A, B, C and D were strong and flexible at room temperature, and when heated to 40° C. became soft and conformal. Sample C had a desirable low melt modulus and high melt elongation. Sample D had a relatively high melt modulus and relatively poor melt elongation. Sample B was transparent, so that a wound covered by it could be inspected without removing the sample.

Examples 18–24

In Examples 18–34, the ingredients and amounts thereof set out in Table 2 were made by melt mixing in a Brabender. The modulus and elongation of the blends in Examples 19–34 were measured.

In Example 22, the polymeric composition (S20+EY901) was hot melt coated as a layer about 0.01 inch (0.025 cm) thick onto the GL Knit fabric. The coated fabric was maintained at 100° C. for 4 hours and cooled. The resulting composite was about 0.07 inch (0.18 cm) thick. The composite was then heated with a hot air gun to soften the polymeric composition, stretched 100%, and cooled in the stretched state. A sample of the cooled fabric, 12 by 48 inch (30.5 by 122 cm) (stretched lengthwise) was wrapped 3 times around a metal tube of 12.7 cm diameter and the exterior wrapped end was bonded to the layer below with a polyamide hot melt adhesive. The wrapped fabric was heated to recover it onto the tube, and after cooling, the expanded cast was pulled off the tube. The cast was placed over a person's wrist and forearm, and heated with a hair dryer. It recovered fully within 100 seconds and after cooling provided a rigid cast.

TABLE 1

SCC POLYMERS

| | S1 | S2 | S3 | S4 | S5 | S6 | S7 | S8 | S9 | S10 | S11 | S12 |
|---|---|---|---|---|---|---|---|---|---|---|---|---|
| Monomers | | | | | | | | | | | | |
| AA | 4 | 4 | — | 4 | 4 | 4 | 4 | 4 | 4 | — | — | 21.1 |
| C4A | — | — | — | 10 | — | — | — | 26 | — | 8 | — | — |
| C14A | — | — | — | — | — | — | — | — | — | — | — | 301 |
| C16A | 48 | 56 | 38 | — | — | — | — | — | — | — | — | 378 |
| C18A | 48 | 40 | 57 | 86 | 86 | 86 | 70 | 70 | 70 | 80 | 90 | — |
| MMA | — | — | — | — | — | 10 | — | — | 26 | 5 | — | — |
| GMA | — | — | 5 | — | — | — | — | — | — | 7 | 10 | — |
| ETGMA | — | — | — | — | — | — | 26 | — | — | — | — | — |
| STY | — | — | — | — | 10 | — | — | — | — | — | — | — |
| Properties | | | | | | | | | | | | |
| Tm (°C.) | 45 | 41 | 46 | 48 | 51 | 50 | 51 | 43 | 38 | 42 | 45 | 29 |
| MWt (10³ D) | 10 | 54 | 97 | 112 | 71 | 87 | 142 | 138 | 60 | 10 | 9 | 398 |

| | S13 | S14 | S15 | S16 | S17 | S18 | S19 | S20 | S21 | S22 | S23 |
|---|---|---|---|---|---|---|---|---|---|---|---|
| Monomers | | | | | | | | | | | |
| AA | 5 | 3 | 4 | 5 | — | 4 | 2 | 3 | 3 | 3 | — |
| C4A | 10 | — | — | — | 10 | — | — | — | — | — | — |
| C14A | — | — | — | — | — | — | — | — | — | — | — |
| C16A | — | — | 40 | — | — | 48 | — | — | — | — | — |
| C18A | 95 | 97 | 60 | 95 | 90 | 48 | 98 | — | — | — | — |
| C22A | — | — | — | — | — | — | — | 60 | 68 | 80 | 55.6 |
| MMA | — | — | — | — | — | — | — | — | — | — | — |
| GMA | — | — | — | — | — | — | — | — | — | — | — |
| ETGMA | — | — | — | — | — | — | — | — | — | — | — |
| STY | — | — | — | — | — | — | — | 37 | 29 | 17 | 41.4 |
| Properties | | | | | | | | | | | |
| Tm (°C.) | — | 47 | 47 | 46 | 45 | — | 46 | 45 | 50 | 55 | 47 |
| MWt (10³ D) | 9 | 5.7 | 9 | 90 | 6.7 | 300 | 57 | 186 | 112 | 138 | 58 |

TABLE 2

COMPOSITIONS AND FABRICS

| Ex. No. | COMPOSITION SCC | Other | Modulus psi | Elongation % | FABRIC |
|---|---|---|---|---|---|
| 1, 2 | S1 (25) | XAMA (0.125) | — | — | NL Knit |
| 3A | S2 (100) | — | — | — | GLF (0.75) |
| 3B | S2 (100) | — | — | — | GLF (1.5) |
| 3C, 4, 5 | S2 (100) | — | — | — | GLF (2.0) |
| 6 | S3 (25) | JT (5) | — | — | NL Knit |
| 7 | S12 (100) | — | — | — | from Example 6 |
| 8 | S3 (25) | JT (5) | — | — | GRAPH |
| 9 | S1 (5) | PCL (5) | — | — | — |
| 10A | S3 (100) | — | — | — | — |
| 10B | S3 (100) | PCL | — | — | — |
| 11 | S1 (6) | ELV240 (6) | — | — | NL Knit |
| 12 | S2 (100) | — | — | — | from Example 3B |
| 13 | S3–S11 (5) | — | — | — | NL Knit |
| 14 | S3 (100) | — | — | — | from Example 6 |
| 15 | S13 (5) | ELV240 (5) | — | — | NL Knit |
| 16A | S14 (5) | ELV240 (5) | — | — | — |
| 16B | S15 (5) | ELV4320 (5) | — | — | — |
| 16C | S16 (5) | ELV150 (5) | — | — | — |
| 16D | S17 (5) | ELV250 (5) | — | — | — |
| 17A | S18 (85) | JT (15) | — | — | — |
| 17B | S18 (80) | JT (20) | — | — | — |
| 17C | S18 (80) | JT (20) | — | — | — |
| 17D | S18 (70) | JT (30) | — | — | — |
| 17E | S18 (100) | — | — | — | — |
| 18 | S19 (50) | ELV4320 (50) | — | — | incompatible |
| 19 | S20 (75) | ELV40 (25) | 20.5 k | 70 | — |
| 20 | S20 (80) | ELV40 (20) | 22.5 k | 38 | — |
| 21 | S20 (75) | ELV4260 (25) | 21.2 k | 51 | — |
| 22 | S20 (75) | EY901 (25) | 33.8 k | 27 | GL Knit |

TABLE 2-continued

COMPOSITIONS AND FABRICS

| Ex. No. | COMPOSITION SCC | Other | Modulus psi | Elongation % | FABRIC |
|---|---|---|---|---|---|
| 23 | S20 (75) | EY902 (25) | 21.2 k | 21 | — |
| 24 | S21 (75) | ELV4320 (25) | | | |
| 25 | S22 (60) | ELV4320 (40) | 21 k | 25 | — |
| 26 | S22 (70) | ELV4320 (25) | 30 k | 3 | — |
| 27 | S20 (100) | — | 48 k | 2.5 | — |
| 28 | S20 (80) | EY901 (20) | 34 k | 27 | — |
| 29 | S20 (60) | ELV4260 (S20) Nytal (20) | 46.2 k | 24 | — |
| 30 | S20 (54) | ELV4260 (18) DAB9 (28) | 41.5 k | 18 | — |
| 31 | S20 (54) | ELV4260 (18) DAB9 (28) | 41.5 k | 18 | — |
| 32 | S20 (58) | ELV4260 (14) DAB9 (28) | 46 k | 34 | — |
| 33 | S20 (60) | ELV4260 (20) DAB9 (20) | 37.4 k | 37 | — |
| 34 | S20 (60) | ELV40 (20) DAB9 (20) | 34.6 k | 37 | — |

Example 25

An expanded cast made by the procedure of Example 24 was slit lengthwise. It opened up to a C-shaped cross-section. Opposite edges of a strip of NL Knit fabric about 1.5 inch (3.8 cm) wide were sewn to the slit edges, securing them together and reclosing the tube. The resulting cast was placed over a person's wrist and forearm, and heated with a hair dryer. It recovered, and, after cooling, provided a cast which was sufficiently rigid to prevent movement, but which could expand or contract to accommodate swelling or shrinkage of the wrist or forearm and which could be removed.

Example 26

The procedure of Example 25 was followed except that, instead of the fabric strip, two halves of a zipper were secured to the slit edges of the cast so that the cast could be secured in place by closing the zipper.

Example 27

The procedure of Example 25 was followed except that, instead of the fabric strip, matching parts of a Velcro closure were secured to the inner and outer surfaces, respectively, adjacent the cut edges, so that the cast could be secured in place by pressing together the matching parts.

Example 28

This example shows the advantages of a cast having an open structure. In each of the tests reported below, a flat sample of an unused cast was placed on a metal screen below the tip of a hot air gun at a distance of about 3 inch (7.6 cm) for samples 1, 2 and 3, and about 5 inch (12.7 cm) for samples 4, 5 and 6. Thermocouples were placed on the top and bottom of the sample, and recorded the temperature at 15 second intervals as the sample was heated by a constant flow of hot air from the gun. The various samples used were:

1. A sheet of PCL 0.03 inch (0.076 cm) thick, without apertures.
2. A composite about 0.048 inch (0.12 cm) thick obtained by melt laminating a sheet of PCL 0.03 inch (0.076 cm) thick, without apertures, and a knitted fiberglass tape.
3. A composite about 0.06 inch (0.15 cm) thick obtained by laminating two layers of composite 2 and expanding the laminate 100%; this composite was highly porous.
4. A sheet of the S20 SCC polymer about 0.043 inch (0.11 cm) thick, without apertures.
5. The expanded composite made in Example 22, which was highly porous.
6. The composite made in Example 22, before it was expanded.

The results obtained are set out in Table 3 below, and clearly show the benefits of the open structure in samples 3 and 5, as compared to the non-porous structures of the other samples.

TABLE 3

| | | Temperature of Sample (°C.) After (secs) | | | | | |
|---|---|---|---|---|---|---|---|
| | | 0 | 15 | 30 | 45 | 60 | 90 |
| Sample 1 | Top | 27 | 61 | 67 | 62 | 61 | — |
| | Bottom | 28 | 40 | 50 | 61* | 62 | — |
| Sample 2 | Top | 26 | 73 | 78 | 76 | 78 | — |
| | Bottom | 25 | 48 | 54 | 62* | 63 | — |
| Sample 3 | Top | 26 | 70 | 78 | — | — | — |
| | Bottom | 26 | 68* | 79 | — | — | — |
| Sample 4 | Top | 24 | 53 | 60 | 67 | 69 | 66 |
| | Bottom | 23 | 36 | 41 | 47 | 52 | 63* |
| Sample 5 | Top | 23 | 68 | 71 | 71 | — | — |
| | Bottom | 23 | 63* | 70 | 70 | — | — |
| Sample 6 | Top | 24 | 64 | 70 | 71 | 74 | — |
| | Bottom | 25 | 42 | 62* | 72 | 62 | — |

*At this time, the cast was recovering and/or moldable

Examples 35–49

In Examples 35–49, the support was made from an elastically extensible fabric which is available from Carolina Narrow Fabrics (Winston Salem, N. C., USA). The fabric is a three bar knitted warp fabric with ECDE 75 110 Z glass fiber yarn in the first and second bars and a 60 gauge monofilament rubber yarn in the third bar. It has a density (unstretched) of 800±100 g/m2 and will return to substantially its original length if stretched by up to about 2.5 times its original length.

The liner is made from a padded stockinette having a flattened width of about 9 cm (i.e. a diameter of about 5.75 cm) which is available from Smith and Nephew Casting (Menomonee Falls, Wis., USA) under the trade name Protouch One-Step and which is a cotton/spandex stockinette with an adhesively bonded polyester padding of low density which can be stretched by the stockinette without tearing.

The polyurethane prepolymer compositions A and B contained the ingredients and amounts thereof (in grams) set out in the table below.

| Ingredients | A | B |
|---|---|---|
| Isonate 143L | 200 | 63 |
| Pluracol P1010 | 188 | 19 |
| Poly G 36-232 | — | 13.5 |
| DABCO | 6 | 2 |
| Benzoyl chloride | 0.2 | 0.1 |
| Polydimethyl siloxane | 0.5 | 0.3 |

Isonate 143 L is available from Dow Chemical (Midland, Mich., USA) and is methylene diphenylene diisocyanate and oligomers thereof Pluracol P1010 is available from BASF Performance Chemicals (Parsippany, N. J., USA) and is polyethylene glycol. Poly G 36-232 is available from Olin Chemicals (Cheshire, Conn., USA) and is a polyether polyol. DABCO is available from Air Products and Chemicals (Allentown, Pa., USA) and is triethylene diamine; it is a catalyst for the polymerization of Isonate 143L and Pluracol P1010. An alternative catalyst is DMDEE (2,2' dimorpholinodiethyl ether), which is available from Texaco Chemicals (Houston, Tex., USA). Benzoyl chloride is an inhibitor. Polydimethyl siloxane is an antifoaming agent which is available from Dow Coming (Midland, Mich., USA) or from Huls America (Bristol, Pa., USA).

Example 35

The casting composition used in Example 35 was a blend of about 80% of an SCC polymer having a $T_m$ of about 50° C. and about 20% of an ethylene/vinyl acetate copolymer (EVA) which is available from du Pont (Wilmington, Del., USA) under the trade name Elvax 210, is reported to contain about 28% vinyl acetate and to have a softening point of about 90° C. The blend has a molecular weight of about 200,000. The SCC copolymer had a molecular weight of about 220,000 and contained units derived from about 68% of dodecyl acrylate (C22A), about 4% acrylic acid (AA), and about 28% of styrene (STY). The blend was made by the following procedure. C22 A (68 parts), STY (28 parts), AA (4 parts) and dodecane thiol (0.04 parts) were mixed. 20 parts of the mixture were heated to about 120° C. The remaining 80 parts were mixed with t-amyl peroxy-2-ethyl hexanoate (0.5 part) and added ova 90 minutes, maintaining the reaction mixture at 120° C. The temperature was raised to 140° C. over a period of about 45 minutes, while adding t-amyl peroxy benzoate (0.5 part). The temperature was maintained at 140° C. for a further 2 hours. EVA (25 parts) and butylated hydroxytoluene (0.3 part) were then added, and the mixture maintained at 40° C. for a further 1–2 hours, with stirring. The blend was then cooled.

The casting composition was heated to a temperature of about 100° C. and was then melt coated onto a length of the support fabric, about 11.4 inch (28.8 cm) long and about 12 inch (30 cm) wide. The coated fabric was maintained at a temperature of about 100° C. for about 4 hours to ensure that the support was thoroughly impregnated by the casting composition, and was then cooled. The coated fabric was reheated by means of a hot air gun to a temperature of about 90° C., stretched to about 2.5 times its original length, and cooled in the stretched state. The stretched fabric was about 28.5 inch (about 72 cm) long and about 12 inch (36 cm) wide, had an open structure with a plurality of apertures each having an area of about 0.02 cm2, and had an AFP of about 15.5%. The cooled, stretched, coated fabric was wrapped three times around a metal mandrel having a circumference of about 9.5 inch (about 24 cm), i.e. a diameter of about 3 inch (about 7 cm), and the outer wrapped end was secured to the layer below with a polyamide hot melt adhesive.

The composite structure was removed from the mandrel. It had an AFP of about 7%. It was flattened and then cut to a shape as shown in FIG. 4 (in which the outer edges of the portions removed are shown by the dotted lines) and having dimensions a, b, c and d approximately as follows: a, 4 cm; b, 3.8 cm; c, 3 cm; and d, 2 cm.

The composite structure was restored to a generally cylindrical shape and a length of the liner fabric was placed inside it. The liner fabric was about 15 inch (38 cm) long, and had a hole about 0.4 inch (1 cm) in diameter punched in it, the center of the hole being about 2.4 inch (about 6 cm) from one end. The centers of the holes in the heat-recoverable main member and the liner were approximately aligned, and the ends of the liner were then stretched radially and folded back over the ends of the main member.

The resulting orthopedic cast could be flattened for storage purposes, and then restored to a generally cylindrical shape before use.

The cast (after being restored to a generally cylindrical shape) was slipped ova a person's hand, wrist and forearm, with the thumb through the holes in the liner and main member, and with the angled end parallel to the palmer creases of the hand. The folded ends of the liner were unfolded over the person's arm and hand. The heat-recoverable main member was then heated with a hot air gun to soften the casting composition and cause recovery of the cast around the wrist and forearm. This took about 2–5 minutes. The liner protected the patient from being burned by the hot air and the heated cast. After the cast had cooled, the ends of the liner were folded back over the cast, thus padding its edges.

Example 36

Example 35 was repeated except that the casting composition was a polycaprolactone composition which is available from Solvay Interox Chemicals (Warrington, Great Britain) under the trade name CAPA 640, and which has a $T_m$ of about 57° C. and a reported molecular weight of about 37,000.

The casts produced in Examples 35 and 36 had similar crush strengths (about 50 lb), but the adhesion between the layers was better in Example 36 than in Example 35. We have found that if the amount of EVA used in Example 35 is increased to about 40%, or if an EVA of higher molecular weight (e.g. Elvax 240) is used, the adhesion between the layers improves.

Example 37

A cooled, stretched, coated fabric was made as in Example 35. A length of the fabric about 4 inch (10 cm wide) was wrapped twice around a metal mandrel having a circumference of about 24 cm, i.e. a diameter of about 7.6 cm, and the outer wrapped end was secured to the layer below with a polyamide hot melt adhesive. The composite structure was removed from the mandrel, placed over a second metal mandrel having a circumference of about 19 cm, i.e. a diameter of about 6 cm, and fully shrunk down onto the second mandrel, using a hot air gun. Its weight was about 25 g.

Example 38

Example 37 was repeated, and the recovered cast, still on the mandrel, was coated with about 10 g of prepolymer composition A. The coating was then sprayed with water, and as a result polymerized, with foaming. The resulting cooled product had a substantially greater crush strength than the product of Example 37.

Example 39

Example 37 was repeated except that before the composite structure was shrunk down onto the second mandrel, it was coated with about 10 g of prepolymer composition A. Just before using the heat gun to shrink the composite structure, the prepolymer layer was sprayed with water. Application of the hot air gun resulted in simultaneous shrinkage of the composite structure and polymerization of the prepolymer. The polymerization mix foamed less and had a lower viscosity during the polymerization than in Example 38. The resulting cooled product had a substantially greater crush strength than the product of Example 38.

Example 40

Example 37 was repeated except that the second mandrel had a circumference of about 14 cm, i.e. a diameter of about 4.5 cm.

Example 41

Example 40 was repeated, and the recovered cast, still on the second mandrel, was coated with about 10 g of prepolymer composition B. The coating was then sprayed with water, and as a result polymerized, with foaming.

Example 42

Example 40 was repeated except that before the composite structure was shrunk down onto the second mandrel, it was coated with about 10 g of prepolymer mixture composition B. Just before using the heat gun to shrink the composite structure, the prepolymer layer was sprayed with water. Application of the hot air gun resulted in simultaneous shrinkage of the composite structure and polymerization of the prepolymer. The polymerization mix foamed less and had a lower viscosity during the polymerization than in Example 41.

Example 43

Example 42 was repeated, taking particular care to ensure a uniform coating of the prepolymer composition.

Example 44

Example 40 was repeated except that a film of the SCC/EVA casting composition, about 0.024 inch (about 0.6 mm) thick, was placed between the wraps of cooled, stretched, coated fabric before the composite structure was recovered by heating. The crush strengths of the products obtained in Examples 41–45 are shown below.

| Example No. | 41 | 42 | 43 | 44 | 45 |
| --- | --- | --- | --- | --- | --- |
| Crush Strength (lb) | 1.7 | 15.2 | 14.4 | 26.2 | 8.1 |

Example 45

The procedure of Example 35 was followed up to the stage at which the composite structure was removed from the mandrel. A piece of the support fabric (19.2×30 cm) impregnated with prepolymer composition B (45% of total weight), was foamed into a tube using a polyamide hot melt adhesive. The tube was stretched and fitted over the composite structure. The resulting assembly was placed over a mandrel (diameter about 4.5 cm) and then heated with a hot air gun at about 70° C. for about 5 minutes so that the cast recovered and conformed to the mandrel. Water was then sprayed onto the cast, causing polymerization of the prepolymer. The finished cast had a substantially greater crush strength than the product of Example 35.

Example 46

Two identical composite structures were made by the procedure of Example 35 except that the expanded support fabric was 48×10 cm and was wrapped twice around the 24 cm mandrel. The first structure was placed over a mandrel (diameter 4.5 cm); and heated in an oven at about 70° C. for about 5 minutes so that it recovered. The second structure was then placed over the first, and heated in an oven at about 70° C. for about 5 minutes so that it recovered.

Example 47

The procedure of Example 46 was followed except that a single composite structure was prepared and recovered.

Examples 48–49

The procedures of Examples 46 and 47, respectively, were followed, except that the casting composition was CAPA 640 as in Example 36.

The crush strengths of the recovered casts in Examples 46–495 are given in the table below.

| Example No. | 46 | 47 | 48 | 49 |
| --- | --- | --- | --- | --- |
| Crush Strength (lb) | 50 | 9.6 | 69 | 26 |

We claim:

1. A heat-shrinkable orthopedic cast which is preshaped and sufficiently oversize to allow it to be placed around a limb of a patient and which, after being placed around the limb, can be heated so that it shrinks towards the limb, the cast comprising
   (1) a heat-shrinkable main member which comprises
   (a) a fabric support which
   (i) is in an elastically stretched condition, and
   (ii) comprises elastic fibers which are composed of an elastomeric material and are elastically stretched, and
   (b) a solid casting composition which (i) comprises a crystalline casting polymer having a crystalline melting point $T_m$, of 40° to 85° C., (ii) contacts the support and maintains it in its elastically stretched condition, and (iii) when the cast is heated to a temperature above $T_m$, softens and permits shrinkage of the heat-shrinkable main member, at least some of the shrinkage of the main member being provided by elastic shrinkage of the elastically stretched fibers, and (2) a liner which comprises padding material and is secured to the inside of the main member.

2. A cast according to claim 1 wherein the support is a knitted fabric which comprises elastomeric yarns and glass fiber yarns.

3. A cast according to claim 1 wherein the liner comprises a tube of elastically deformed stockinette fabric.

4. A cast according to claim 1 wherein the liner has an air flow permeability of less than 25%.

5. A cast according to claim 1 wherein $T_m$ is 45° to 85° C.

6. A cast according to claim 5 wherein the crystalline polymer is polycaprolactone.

7. A cast according to claim 1 wherein the heat-shrinkable main member has a plurality of apertures through its thickness, each of the apertures having an area of 0.01 to 0.12 cm$^2$.

8. A cast according to claim 1 wherein the heat-shrinkable main member has a plurality of apertures through its thickness and has an air flow permeability of 10 to 60%.

9. A cast according to claim 1 wherein the liner has an air flow permeability which is less than 0.75 times the air flow permeability of the heat-shrinkable main member.

10. A cast according to claim 1 wherein the padding material in the liner comprises a non-woven fabric of cellulosic or polyester fibers.

11. A cast according to claim 1 wherein the padding material in the liner comprises a foamed polymer.

12. A heat-shrinkable orthopedic cast which is preshaped and sufficiently oversize to allow it to be placed around a limb of a patient and which, after being placed around the limb, can be heated so that it shrinks towards the limb, the cast comprising (1) a heat-shrinkable main member which comprises
  (a) a fabric support which
    (i) is in an elastically stretched condition, and
    (ii) comprises elastic fibers which are composed of an elastomeric material and are elastically stretched, and
  (b) a solid casting composition which (i) comprises a crystalline casting polymer having a crystalline melting point, $T_m$, of 40° to 85° C., (ii) contacts the support and maintains it in its elastically stretched condition, and (iii) when the cast is heated to a temperature above $T_m$, softens and permits shrinkage of the heat-shrinkable main member, at least some of the shrinkage of the main member being provided by elastic shrinkage of the elastically stretched fibers, and (2) a flexible reinforcing component which (a) does not prevent shrinkage of the main member, (b) has been applied to the main member and, (c) comprises a polymer precursor which can be polymerized to form a relatively rigid component.

13. A cast according to claim 12 wherein the polymer precursor is a water-hardenable polyurethane precursor.

14. A cast according to claim 12 which comprises a second elastically deformed support which is stretched over the heat-shrinkable main member and which supports the polymer precursor.

15. A cast according to claim 12 which is stored in a moisture-impermeable envelope.

16. A cast according to claim 12 which, after recovery by means of a heat gun, has a crush strength which is at least 1.5 times the crush strength of a cast which has been recovered in the same way and which is identical except that it does not contain the reinforcing component.

17. A cast according to claim 12 which, after recovery by means of a heat gun, has a crush strength which is at least 5 times the crush strength of a cast which has been recovered in the same way and which is identical except that it does not contain the reinforcing component.

18. A cast according to claim 12 wherein the casting polymer is polycaprolactone.

19. A heat-shrinkable orthopedic cast which is preshaped and sufficiently oversize to allow it to be placed around a limb of a patient and which comprises (1) a fabric support which
  (a) is in an elastically stretched condition, and
  (b) comprises elastic fibers which are
    (i) composed of an elastomeric material and
    (ii) elastically stretched; and (2) a solid casting composition which
  (a) comprises a crystalline polymer having a crystalline melting point $T_m$ which is at least 40° C. and no more than 60°,
  (b) contacts the fabric support and maintains it in its elastically stretched condition, and
  (c) when the cast is heated to a temperature above $T_m$ after the cast has been placed around a limb of a patient, softens into an amorphous state and permits shrinkage of the cast towards the limb without exposing the patient to a temperature which cannot be safely tolerated by the patient;

said cast, when heated to a temperature above $T_m$ and permitted to shrink in the absence of any restraint, having at least one dimension which shrinks by more than about 5% based on that dimension prior to heating, at least some of the shrinkage of the cast, when it is heated, being provided by elastic shrinkage of the elastically stretched fibers of the fabric support.

20. A cast according to claim 19 wherein $T_m$ is at least 45° C.

21. A cast according to claim 19 wherein the casting polymer comprises a polycaprolactone.

22. A cast according to claim 19 wherein the casting composition comprises an SCC polymer and a polycaprolactone.

23. A cast according to claim 19 wherein the support, in the absence of the casting composition, can be stretched elastically by at least 25%, based on the corresponding dimension of the support in its unstretched state.

24. A cast according to claim 23 wherein the support is a knitted fabric which comprises yarns composed of an elastomeric material.

25. A cast according to claim 24 wherein the support is knitted from at least one elastomeric yarn and at least one glass fiber yarn.

26. A cast according to claim 19 wherein at least part of the article has a plurality of apertures through its thickness, each of the apertures having an area of 0.01 to 0.08 cm$^2$.

27. A cast according to claim 19 wherein at least part of the article has air flow permeability of 10 to 35%.

28. A cast according to claim 19 which comprises at least two layers of the elastomeric support.

29. A cast according to claim 19 which comprises (A) a heat-recoverable section which comprises the stretched support and the casting composition, and (B) an elastically deformable elastomeric section which is free of the casting composition.

30. A cast according to claim 19 wherein the shrinkage of the cast, when it is heated, is provided substantially entirely by elastic recovery of the elastically stretched fibers in the fabric support.

31. A cast according to claim 19 wherein the support is a knitted fabric having a power of 0.1 to 2 lb/inch.

32. A cast according to claim 19 which, when heated to a temperature above $T_m$ and permitted to shrink in the absence of any restraint, has at least one dimension which shrinks by 25 to 62% based on that dimension prior to heating.

33. A cast according to claim 19 which, when heated to a temperature above $T_m$ and permitted to shrink in the absence of any restraint, followed by cooling to 25° C., has a strength of more than 5 lb/inch.

34. A cast according to claim 19 wherein the casting composition comprises (A) a random copolymer which comprises
  (i) at least 30% of units having a crystalline melting point (in the copolymer) of $T_m$°C. and derivable from at least one n-alkyl acrylate or n-alkyl methacrylate wherein the n-alkyl group contains 14 to 50 carbon atoms, and
  (ii) 7 to 70% of units derived from at least one monomer, said monomer being one which, when homopolymerized, results in a homopolymer having a glass transition point $T_g$ which is at least $(T_m+10)$ °C., and (B) a random copolymer which comprises
  (i) at least 30% of units derived from ethylene and
  (ii) 7 to 70% of units derived from an ethylenically unsaturated monomer containing at least one polar group, the ratio of A to B being from 0.25 to 4.

35. A cast according to claim 19 wherein the casting composition comprises (A) an SCC polymer which has a molecular weight of less than 15,000 and which contains 2 to 10% of units derived from acrylic or methacrylic acid, and (B) an ethylene/vinyl acetate copolymer which contains 25 to 40% of units derived from vinyl acetate.

36. A cast according to claim 19 wherein the casting composition comprises the reaction product of (A) 30 to 90% of at least one SCC polymer having a crystalline melting point $T_m$ (in the composition) of 40° to 60° C., and (B) 10 to 70% of at least one amorphous polymer which (i) contains a plurality of groups which react with the SCC polymer and (ii) has a molecular weight of 1,000 to 20,000.

37. A cast according to claim 19 which is in the form of a cylinder and is suitable for use as a finger splint.

38. A cast according to claim 19 which is in the form of a bent cylinder and is suitable for use as a cast around an ankle, knee or elbow.

39. A cast according to claim 19 which is in the form of a glove and is suitable for use as a cast around a hand.

* * * * *